US012570594B2

(12) United States Patent
Li et al.

(10) Patent No.: US 12,570,594 B2
(45) Date of Patent: Mar. 10, 2026

(54) METHOD FOR PARTIALLY OXIDIZING ALKANE

(71) Applicant: Japan Science and Technology Agency, Kawaguchi (JP)

(72) Inventors: Xiaohong Li, Kitakyushu (JP); Hiroyuki Imai, Kitakyushu (JP); Yang Song, Kitakyushu (JP); Atsushi Takagaki, Fukuoka (JP); Kyoko Bando, Tsukuba (JP); Junichi Murakami, Tsukuba (JP); Toshitaka Kubo, Tsukuba (JP); Tetsuya Kodaira, Tsukuba (JP)

(73) Assignee: Japan Science and Technology Agency, Kawaguchi (JP)

( * ) Notice: Subject to any disclaimer, the term of this patent is extended or adjusted under 35 U.S.C. 154(b) by 566 days.

(21) Appl. No.: 18/012,334

(22) PCT Filed: Jun. 30, 2021

(86) PCT No.: PCT/JP2021/024713
§ 371 (c)(1),
(2) Date: Dec. 22, 2022

(87) PCT Pub. No.: WO2022/004778
PCT Pub. Date: Jan. 6, 2022

(65) Prior Publication Data
US 2023/0257334 A1 Aug. 17, 2023

(30) Foreign Application Priority Data
Jun. 30, 2020 (JP) ................................. 2020-113160

(51) Int. Cl.
*C07C 45/28* (2006.01)
*B01J 21/04* (2006.01)
*B01J 21/06* (2006.01)
*B01J 29/44* (2006.01)

(52) U.S. Cl.
CPC ............... *C07C 45/28* (2013.01); *B01J 21/04* (2013.01); *B01J 21/066* (2013.01); *B01J 29/44* (2013.01)

(58) Field of Classification Search
CPC ......... C07C 45/28; B01J 21/04; B01J 21/066; B01J 29/44
See application file for complete search history.

(56) References Cited

U.S. PATENT DOCUMENTS

| | | | |
|---|---|---|---|
| 3,996,294 A | 12/1976 | Imre et al. | |
| 4,738,946 A | 4/1988 | Yamashita et al. | |
| 4,906,176 A | 3/1990 | Yamashita et al. | |
| 7,364,712 B2 | 4/2008 | Ohtsuka et al. | |
| 9,314,776 B2 * | 4/2016 | Zhang | B01J 23/46 |
| 2002/0183559 A1 | 12/2002 | Carter | |
| 2004/0013591 A1 | 1/2004 | Ohtsuka et al. | |
| 2020/0024295 A1 | 1/2020 | Muresan et al. | |

FOREIGN PATENT DOCUMENTS

| | | |
|---|---|---|
| CN | 101239310 A | 8/2008 |
| CN | 101239316 A | 8/2008 |
| CN | 103801327 A | 5/2014 |
| CN | 104549339 A | 4/2015 |
| CN | 110639547 A | 1/2020 |
| JP | S6012132 A | 1/1985 |
| JP | H109141096 A | 6/1997 |
| JP | H11165070 A | 6/1999 |
| JP | 2000210564 A | 8/2000 |
| JP | 2000342964 A | 12/2000 |
| JP | 2007098250 A | 4/2007 |
| JP | 2008246473 A | 10/2008 |
| JP | 2010095510 A | 4/2010 |

(Continued)

OTHER PUBLICATIONS

Novoveska, Katerina et al., "Oxidation of propane with oxygen, nitrous oxide and oxygen/nitrous oxide mixture over Co- and Fe-zeolites", Catalysis Today, Feb. 2005, p. 315-319, vol. 100, No. 3-4.
Barbero, J.A. et al., "Breakthrough in the direct conversion of methane into c1-oxygenates", Chem Commun, 2002, pp. 1184-1185.
Li, et al., "Partial Oxidation from Methane to Formaldehyde Using PdmRunOx/Al2O3 Catalyst", Proceeding of the Catalysis Society of Japan, Mar. 2021, p. ROMBUNNO.2P24, vol. 127 (Japanese bibliographical data only).

(Continued)

*Primary Examiner* — Sikarl A Witherspoon
(74) *Attorney, Agent, or Firm* — The Webb Law Firm

(57) ABSTRACT

[Solution] The present invention relates to a method for partially oxidizing an alkane, including contacting an alkane with a supported catalyst in a presence of an oxidizer to convert the alkane into an aldehyde, wherein the supported catalyst is composed of a bimetallic oxide and a support carrying the bimetallic oxide, and the bimetallic oxide is represented by the following formula and includes oxygen and two metals selected from metals of groups 8 to 10 of the periodic table:

$$A_m B_n O_x$$

wherein the bimetallic oxide and support are each a metal selected from metallic elements of groups 8 to 10 of the periodic table; the bimetallic oxide and support are not the same metallic element; m, n, and x mean amounts ((mmol)) of the bimetallic oxide, the support, and oxygen, respectively, per 1 g of the supported catalyst; m is more than 0 [mmol/g-cat] and less than 1 [mmol/g-cat]; n is more than 0 [mmol/g-cat] and less than 1 [mmol/g-cat]; and x is a value [mmol/g-cat] satisfying oxidation states of the bimetallic oxide and the support.

10 Claims, 3 Drawing Sheets

(56)                  References Cited

FOREIGN PATENT DOCUMENTS

| | | | |
|---|---|---|---|
| JP | 2019030827 | A | 2/2019 |
| RU | 2485088 | C1 | 6/2013 |
| WO | 0240152 | A1 | 5/2002 |
| WO | 2020016614 | A1 | 1/2020 |
| WO | 2021002477 | A1 | 1/2021 |

OTHER PUBLICATIONS

Shapovalova, L.B. et al., "CO2 reforming of methane on Ru-Co/
Al2O3-catalyst," Izvestiya Natsional'noi Akademii Nauk Respubliki
Kazakhstan, Seriya Khimicheskaya, 2006, pp. 14-16, vol. 2.
Martinez-Navarro, Blanca, et al., "(Ag)Pd-Fe3O4 Nanocomposites
as Novel Catalysts for Methane Partial Oxidation at Low Tempera-
ture", Nanomaterials, 2020, vol. 10, No. 988.

\* cited by examiner

[Fig. 1]
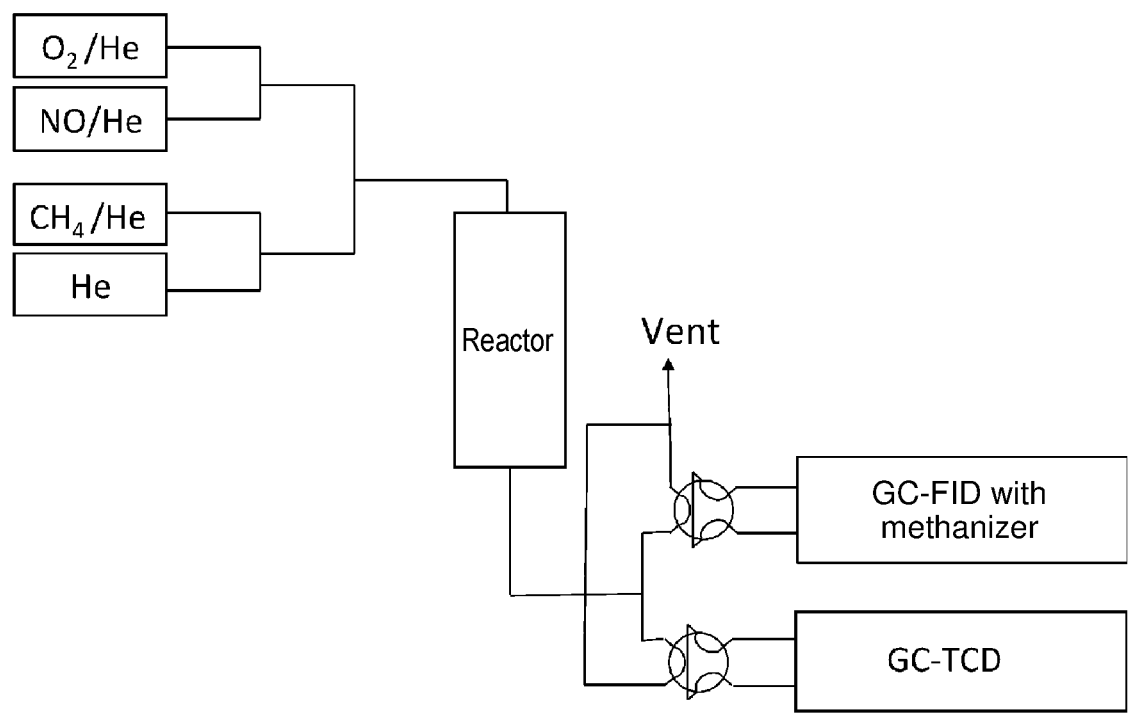
[Fig. 2]
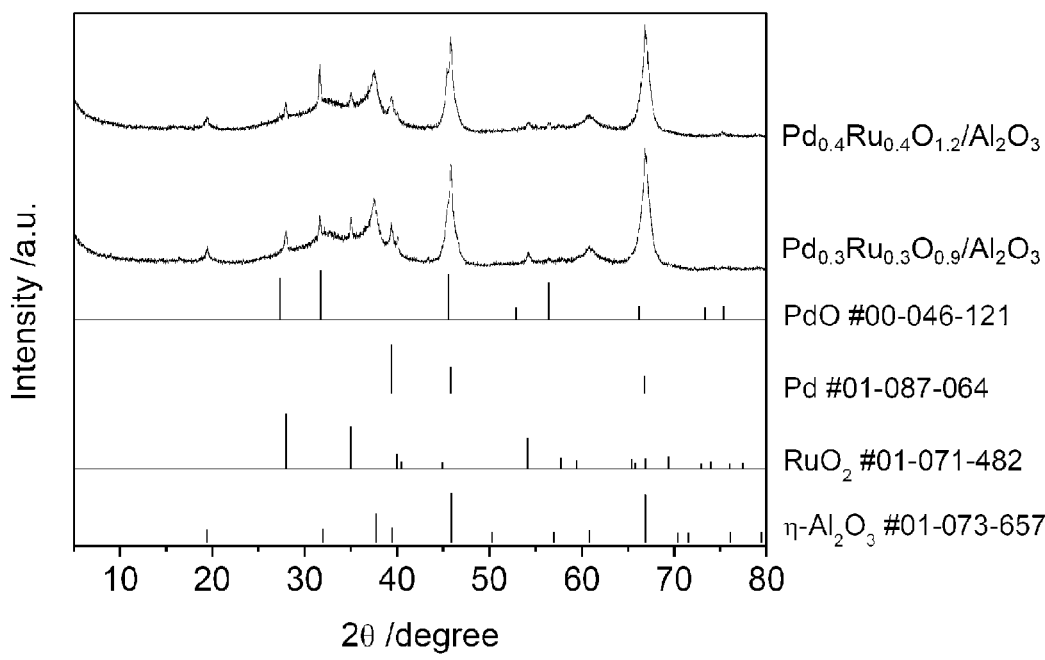

[Fig. 3]
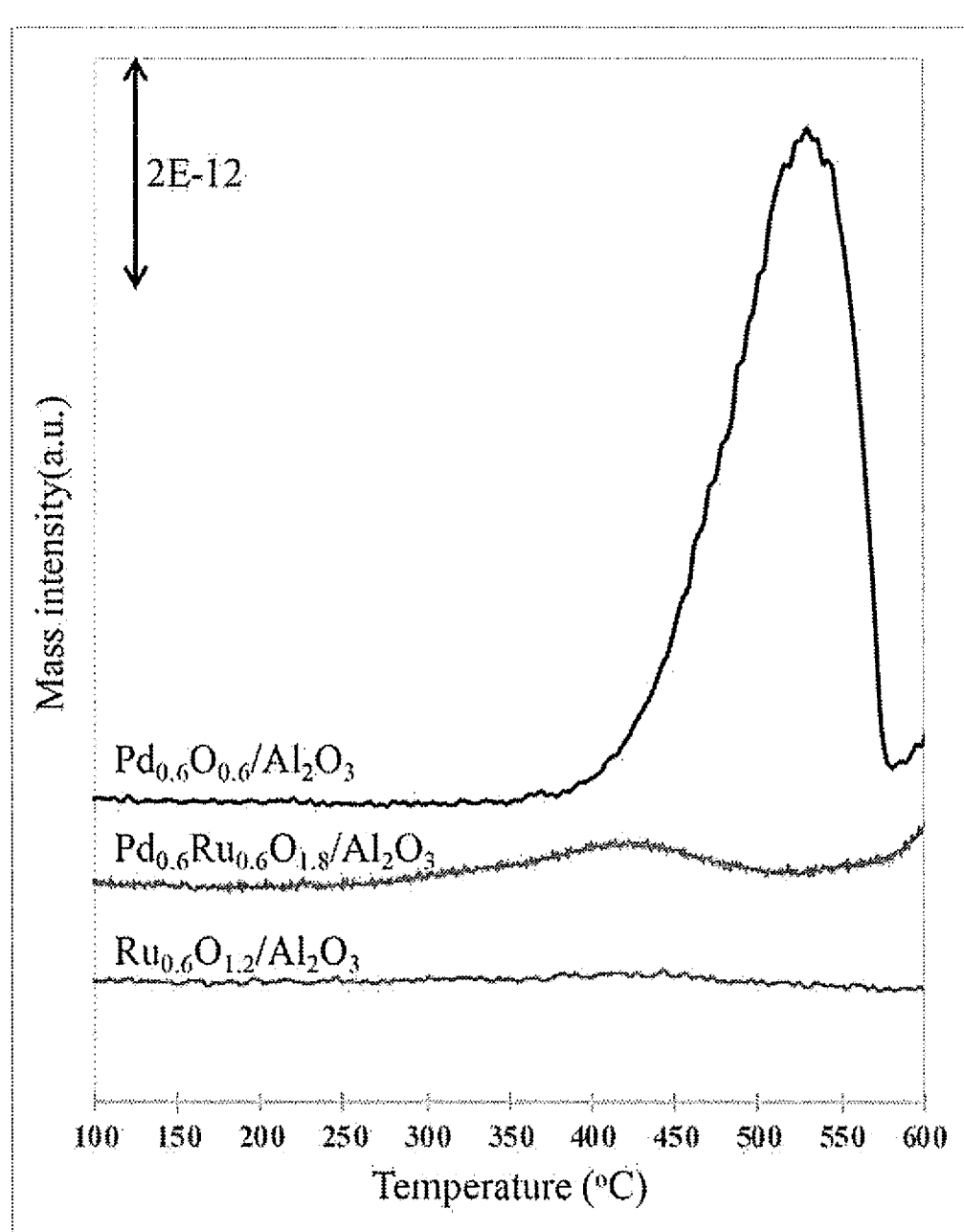

[Fig. 4]
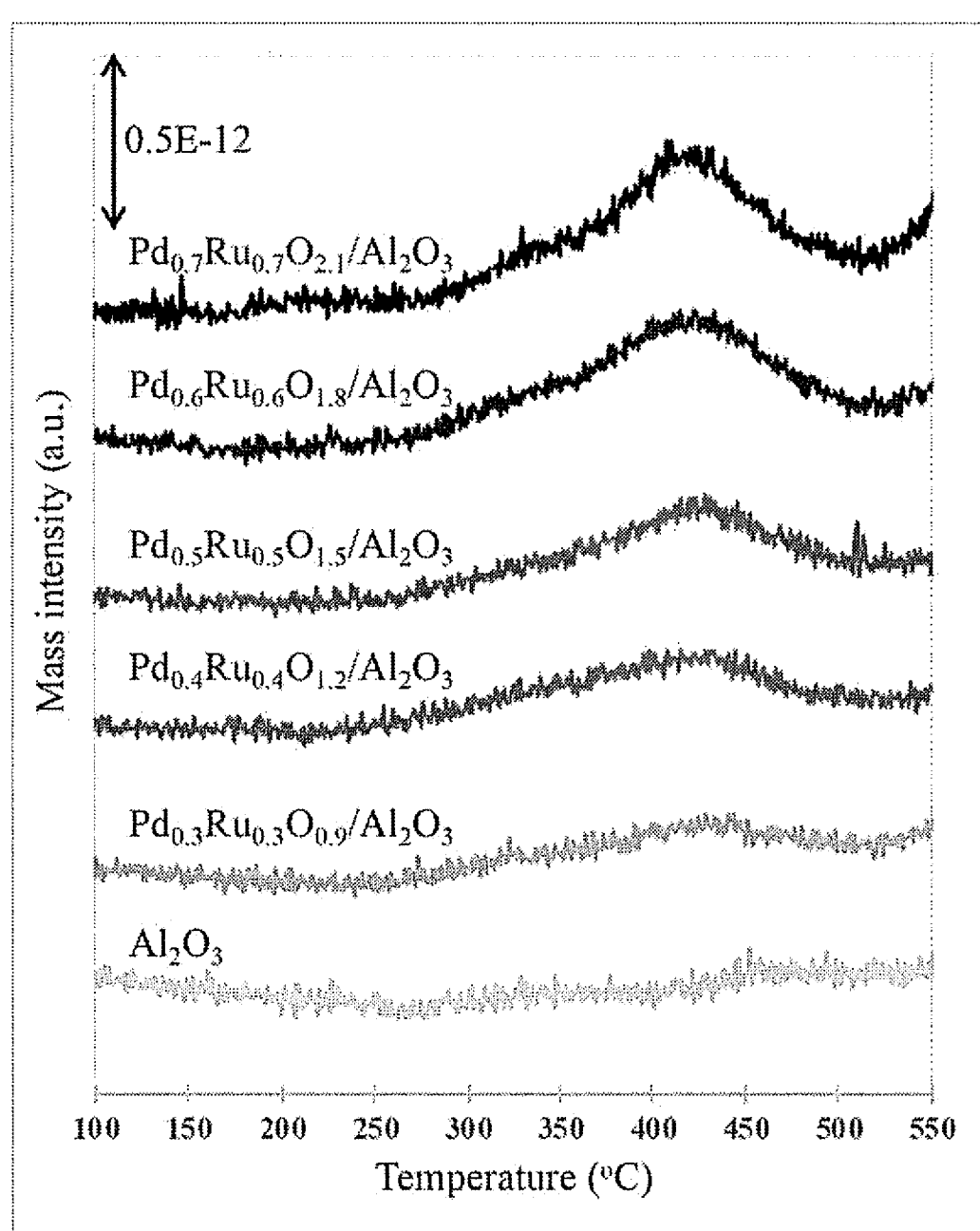

METHOD FOR PARTIALLY OXIDIZING ALKANE

CROSS REFERENCE TO RELATED APPLICATIONS

This application is the United States national phase of International Application No. PCT/JP2021/024713 filed Jun. 30, 2021, and claims priority to Japanese Patent Application No. 2020-113160 filed Jun. 30, 2020, the disclosures of which are hereby incorporated by reference in their entireties.

BACKGROUND OF THE INVENTION

Field of the Invention

The present invention relates to a method for partially oxidizing an alkane.

Description of Related Art

For example, a natural gas, which is in vast reserves, includes an alkane gas resource such as methane, and if the alkane gas resource can be easily converted into a chemical product or energy by an unprecedented technique, the overcoming of the problems of dependence on oil, which the contemporary society confronts, and the reduction in the emission of carbon dioxide can be attained. In addition, methane itself has a global warming potential of 25, and methane naturally occurs from, for example, livestock industry or residues from ethanol fermentation. Taking these into account, effective utilization thereof is important.

Meanwhile, a process for directly converting the alkane gas resource such as methane into, for example, a chemical product is difficult. For example, for partial oxidation of methane to synthesize formaldehyde, which is expected as a starting material for various chemical substance, a multistep process is common in the current situation, in which methane is converted into formaldehyde through carbon monoxide and methanol, and such a process is commercialized. However, this process involves a multistep reaction at a high temperature and a high pressure, and although the process is profitable in an extensive gas field, the process is not efficient in a distributed small-scale facility that generates methane, such as a livestock farm and residues from bioethanol fermentation. Aldehydes such as formaldehyde have various applications.

For example, formaldehyde is used as a starting material for, for example, chemical products, resins, and various techniques for producing an aldehyde have been studied heretofore.

For example, Patent Literature 1 (i.e., JPH9-141096A) suggests, for example, a catalyst for partial oxidation of a saturated hydrocarbon, the catalyst composed of ruthenium oxide and an alkaline earth metal oxide, and a method for partially oxidizing a saturated hydrocarbon with the catalyst, and also suggested that the partially oxidizing is carried out at 300 to 600° C. with the catalyst for partial oxidation. Patent Literature 1 discloses in Examples that formaldehyde is obtained from methane.

Patent Literature 2 (i.e., WO2021/02477) suggests a method in which a hydrocarbon such as methane is contacted with a mixed gas including NO gas, $NO_2$ gas, and $O_2$ gas in the presence of a catalyst to thereby oxidize the hydrocarbon into, for example, an ether or an aldehyde. Patent Literature 2 discloses, as examples of the catalyst, a precious metal or a base metal carried on a support; a combination of a precious metal and another precious metal carried on a support; a combination of a base metal and another base metal carried on a support; or a combination of a precious metal and a base metal carried on a support.

SUMMARY OF INVENTION

Technical Problem

When formaldehyde is produced from methane by conventional techniques, formaldehyde cannot be obtained with a high selectivity. For example, Patent Literature 1 discloses in Examples 3 and 4, in which ruthenium oxide was used, that formaldehyde was obtained at a low temperature of 300° C. or lower with a selectivity of 2.0 to 23.5%, which is a low selectivity. In addition, it is considered for Patent Literature 1 that methane is also converted into other components than formaldehyde, specifically, mainly into $CO_2$. $CO_2$ is difficult to use as, for example, a starting material for a chemical product, and is also one of greenhouse gases, and the reduction in the emission thereof is needed.

The present invention has been made in view of these issues, and an object thereof is to provide a method for partially oxidizing an alkane, the method enabling production of an aldehyde from an alkane with a high selectivity even at a reaction temperature as relatively low as about 300° C.

Solution to Problem

As a result of diligent studies for solving the above-described problems, the present inventors have found a method for partially oxidizing an alkane that can solve the problems, and have completed the present invention.

Specifically, the present invention relates to [1] to [10] below.

[1] A method for partially oxidizing an alkane, comprising the step of contacting an alkane with a supported catalyst (C) in a presence of an oxidizer to convert the alkane into an aldehyde, wherein the supported catalyst (C) comprises a bimetallic oxide (A) carried on a support (B), and the bimetallic oxide (A) is represented by the following formula (1) and includes oxygen and two metals selected from metals of groups 8 to 10 of the periodic table:

$$A_m B_n O_x \tag{1}$$

wherein A and B are each a metallic element selected from metallic elements of groups 8 to 10 of the periodic table; A and B are not the same metallic element; m, n, and x mean amounts ((mmol)) of A, B, and oxygen, respectively, per 1 g of the supported catalyst (C); m is more than 0 [mmol/g-cat] and less than 1 [mmol/g-cat]; n is more than 0 [mmol/g-cat] and less than 1 [mmol/g-cat]; and x is a value [mmol/g-cat] satisfying oxidation states of A and B.

[2] The method for partially oxidizing an alkane according to [1], wherein the two metals selected from metals of groups 8 to 10 of the periodic table are two metals selected from palladium, ruthenium, iridium, and platinum.

[3] The method for partially oxidizing an alkane according to [1] or [2], wherein the contacting of the alkane is performed further in a presence of a solid acid (D).

[4] The method for partially oxidizing an alkane according to any one of [1] to [3], wherein the support (B) is at least one support selected from zeolite, $Al_2O_3$, $TiO_2$, $ZrO_2$, $CeO_2$, $SiO_2$, and $SiO_2—Al_2O_3$.

[5] The method for partially oxidizing an alkane according to any one of [1] to [4], wherein the alkane is methane, and the aldehyde is formaldehyde.

[6] The method for partially oxidizing an alkane according to any one of [1] to [5], wherein the oxidizer is at least one oxidizer selected from oxygen, nitrogen monoxide, and nitrogen dioxide.

[7] The method for partially oxidizing an alkane according to any one of [1] to [6], wherein the partially oxidizing is performed at a temperature of 235 to 350° C.

[8] The method for partially oxidizing an alkane according to any one of [1] to [7], wherein a hybrid catalyst (E) comprising the supported catalyst (C) with a solid acid (D) is used.

[9] The method for partially oxidizing an alkane according to [8], wherein the ratio of the solid acid (D) is 5 to 60 mass % based on 100 mass % in total of the supported catalyst (C) and the solid acid (D).

[10] The method for partially oxidizing an alkane according to [8] or [9], wherein the support (B) of the supported catalyst (C) is at least one selected from $Al_2O_3$, $TiO_2$, $ZrO_2$, $CeO_2$, $SiO_2$, and $SiO_2$—$Al_2O_3$, and the solid acid (D) is at least one selected from ZMS-5 zeolite and USY zeolite; or the support (B) of the supported catalyst (C) is ZMS-5 zeolite, and the solid acid (D) is at least one of $Al_2O_3$ or $ZrO_2$.

Advantageous Effects of Invention

The method of the present invention for partially oxidizing an alkane is a method that can convert an alkane into an aldehyde with a high selectivity and also is completed in a single step at a low temperature and a low pressure. Accordingly, the method can be effectively utilized even for a gas resource from, for example, a distributed small-scale facility that generates methane, and is thus a technique that can sufficiently contribute to the reduction in the emission of greenhouse gases. In addition, methane is present extensively and thinly in such a small-scale facility that generates methane, and then if the method of the present invention is combined with a technique of collecting methane by an adsorption method, methane can be processed more efficiently.

BRIEF DESCRIPTION OF DRAWINGS

FIG. 1 shows a schematic diagram of a fixed-bed flow reaction system used in Experimental Examples.

FIG. 2 shows the analytical results of X-ray crystal diffractometry of $Pd_{0.4}Ru_{0.4}O_{1.2}/Al_2O_3$, $Pd_{0.3}Ru_{0.3}O_{0.9}/Al_2O_3$, PdO, Pd, $RuO_2$, and $\eta$-$Al_2O_3$.

FIG. 3 shows the measurement results of $O_2$-TPD of $Pd_{0.6}Ru_{0.6}O_{1.8}/Al_2O_3$, $Pd_{0.6}O_{0.6}/Al_2O_3$, and $Ru_{0.6}O_{1.2}/Al_2O_3$.

FIG. 4 shows the measurement results of $O_2$-TPD of $Pd_{0.3}Ru_{0.3}O_{0.9}/Al_2O_3$, $Pd_{0.4}Ru_{0.4}O_{1.2}/Al_2O_3$, $Pd_{0.5}Ru_{0.5}O_{1.5}/Al_2O_3$, $Pd_{0.6}Ru_{0.6}O_{1.8}/Al_2O_3$, $Pd_{0.7}Ru_{0.7}O_{2.1}/Al_2O_3$, and $Al_2O_3$.

DESCRIPTION OF THE INVENTION

Next, the present invention will be specifically described.

The method of the present invention for partially oxidizing an alkane is a method for partially oxidizing an alkane, including contacting an alkane with a supported catalyst (C) in a presence of an oxidizer to convert the alkane into an aldehyde, wherein the supported catalyst (C) includes a bimetallic oxide (A) carried on a support (B), and the bimetallic oxide (A) is represented by the following formula (1) and includes oxygen and two metals selected from metals of groups 8 to 10 of the periodic table.

$$A_m B_n O_x \tag{1}$$

In the formula (1), A and B are each a metal selected from metallic elements of groups 8 to 10 of the periodic table; A and B are not the same metallic element; m, n, and x mean amounts ((mmol)) of A, B, and oxygen, respectively, per 1 g of the supported catalyst (C); m is more than 0 [mmol/g-cat] and less than 1 [mmol/g-cat]; n is more than 0 [mmol/g-cat] and less than 1 [mmol/g-cat]; and x is a value [mmol/g-cat] satisfying oxidation states of A and B.

(Alkane and Aldehyde)

In the present invention, the alkane is partially oxidized so that an aldehyde can be obtained. The alkane is preferably an alkane having 1 to 20 carbon atoms, and more preferably an alkane having 1 to 10 carbon atoms. Although the alkane may be branched, the alkane is preferably methane or a linear alkane, and more preferably methane, ethane, or propane, and the alkane is most preferably methane in view of the reaction temperature, the conversion ratio, and the selectivity.

The aldehyde to be obtained by the method of the present invention is an aldehyde that has the same number of carbon atoms and the same carbon skeleton as those of the alkane used as the starting material. Specifically, when methane is used as the alkane, formaldehyde can be obtained, and when ethane is used as the alkane, acetaldehyde can be obtained.

The supported catalyst (C), the oxidizer, the reaction conditions, and others used in the present invention will be described in detail.

(Supported Catalyst (C))

The supported catalyst (C) used for the partial oxidation includes the bimetallic oxide (A) carried on a support (B), and the bimetallic oxide (A) is represented by the following formula (1) and includes oxygen and two metals selected from metals of groups 8 to 10 of the periodic table.

$$A_m B_n O_x \tag{1}$$

In the formula (1), A and B are each a metal selected from metallic elements of groups 8 to 10 of the periodic table; A and B are not the same metallic element; m, n, and x mean amounts ((mmol)) of A, B, and oxygen, respectively, per 1 g of the supported catalyst (C); m is more than 0 [mmol/g-cat] and less than 1 [mmol/g-cat]; n is more than 0 [mmol/g-cat] and less than 1 [mmol/g-cat]; and x is a value [mmol/g-cat] satisfying oxidation states of A and B.

Although a solid acid (D) may be used together with the supported catalyst (C) in the present invention as described later, "cat" in the unit [mmol/g-cat] in the present invention means the supported catalyst (C), and [mmol/g-cat] means the amount ((mmol)) per 1 g of the supported catalyst (C) as stated above. The weight of the solid acid (D) is not included in "cat", and the total amount of the support (B) and the bimetallic oxide (A) corresponds to the weight of the supported catalyst (C).

The two metals selected from metals of groups 8 to 10 of the periodic table is preferably two metals selected from palladium, ruthenium, iridium, platinum, osmium, and rhodium, and preferably two metals selected from palladium, ruthenium, iridium, and platinum.

Examples of the combination of the two metals selected from metals of groups 8 to 10 of the periodic table include a combination of palladium (Pd) as A and ruthenium (Ru) as B in the formula (1); a combination of iridium (Ir) as A and Ru as B in the formula (1); a combination of Pd as A and Ir as B in the formula (1); a combination of platinum (Pt) as A and Ru as B in the formula (1); and a combination of Pt as A and Ir as B in the formula (1). Among these, a combination of palladium (Pd) as A and ruthenium (Ru) as B in the formula (1) is preferable in view of a high selectivity for aldehyde. A metal oxide including a single kind of metallic element as in Patent Literature 1 often tends to bring about a high conversion ratio of the alkane but a low selectivity for aldehyde.

The supported catalyst (C) includes the bimetallic oxide (A) in an amount represented in the formula (1), and m is preferably 0.1 to 0.9 [mmol/g-cat], and more preferably 0.2 to 0.8 [mmol/g-cat]. n is preferably 0.1 to 0.9 [mmol/g-cat], and more preferably 0.2 to 0.8 [mmol/g-cat]. x is a value satisfying oxidation states of A and B, and x is generally 0.3 to 2.7 [mmol/g-cat], preferably 0.6 to 2.4 [mmol/g-cat], but not limited thereto.

m, n, and x can be determined from the weight ratio between starting materials for the bimetallic oxide (A) used when the catalyst is allowed to be carried on the support (B).

The supported catalyst (C) preferably includes 4 to 12 mass %, more preferably 6 to 8 mass %, of the bimetallic oxide (A), based on 100 mass % of the supported catalyst (C).

(Support (B))

The support (B) is not particularly limited as long as the support (B) can carry the bimetallic oxide (A) and be used when partially oxidizing the alkane, and an inorganic oxide is preferably used, which may function as a solid acid. As the inorganic element used for the inorganic oxide support, those of groups 1 to 4 and 13 to 15 of the periodic table can be used. In the structure of the inorganic oxide, it is important that the structure X—O—X is included, wherein X is the element selected. While the inventors do not intend to be bound to the following specific theory, it is considered that the structure of the support (B) contributes to a moderate oxidation of the alkane with the bimetallic oxide (A) carried on the support (B). Specifically, it is considered that the oxygen spices that contributes to moderate oxidation reaction is derived from the bimetallic oxide (A) carried on such a support or the support (B) in the state where the support carries the bimetallic oxide, and that the resulting oxygen defect in the bimetallic oxide (A) or the support (B) is filled by the oxidizer supplied to the reaction system. It is then considered that oxidative dehydrogenation of an alcohol as an intermediate is caused on such a support (B), and thus the reaction easily proceeds toward the generation of the aldehyde.

As such a support, at least one support selected from zeolite, $Al_2O_3$, $TiO_2$, $ZrO_2$, $CeO_2$, $SiO_2$, and $SiO_2$—$Al_2O_3$ is preferable, for example, and at least one support selected from zeolite, $Al_2O_3$, $TiO_2$, $ZrO_2$, and $SiO_2$—$Al_2O_3$ is preferable in view of the yield and others. Even when $CeO_2$ or $SiO_2$ is used, the yield and others can be increased if it is combined with a solid acid.

As alumina, any of α-, γ-, or η-alumina may be used, for example, and γ- or η-alumina is preferably used.

As the zeolite, various zeolites can be used, including, but not particularly limited to, those having a basic skeleton of ZSM-5 zeolite, USY zeolite (Ultra-stable Y zeolite), beta zeolite, Y zeolite, mordenite zeolite, and SAPO zeolite.

As the USY zeolite, zeolite obtained by secondarily processing Y zeolite (Na—Y) can be used, including SUSY (Super Ultrastable Y), VUSY (Very Ultrastable Y), and SDUSY (Super dealuminated ultrastable Y).

As the zeolite, at least one zeolite selected from ZSM-5 zeolite, USY zeolite (ultrastable Y zeolite), and beta zeolite is preferable in view of the pore diameter and the structure, and zeolite that is available under the name of, for example, ZSM-5, USY, or β(38) is more preferable.

The silica/alumina ratio ($SiO_2/Al_2O_3$ (molar ratio)) of the zeolite is generally 3 to 1000, preferably 5 to 800, more preferably 7 to 600, and even more preferably 10 to 400.

For example, as in ZSM-5 (50), a parenthesized numerical value may follow the name of zeolite ((50) in the mentioned example), in the present invention. This means that the silica/alumina ratio ($SiO_2/Al_2O_3$ (molar ratio)) is the numerical value in the parentheses. The silica/alumina ratio is not particularly limited in the present invention.

For the support (B), measures generally used as the standards for performance evaluation of a support used as a support for a catalyst, specifically, the average particle size, the pore size, and the specific surface area, can be referred, and a support in the best condition is selected according to, for example, the substrate for the catalyst, the reaction temperature, the product, and the kind of the catalyst. These measures can be found by known measurement methods. The average particle size can be measured with, for example, a particle size distribution analyzer, the pore size can be measured through, for example, observation under such as an electron microscope, and the specific surface area can be measured using BET method, for example. As the support (B), a support generally having an average particle size of 1 to 1000 μm, and preferably 10 to 500 μm, can be used, for example. The pore size varies depending on what part of the pore is observed, so that care should be taken therefor, and the maximum size is generally 1 to 1000 nm, and preferably 10 to 500 nm. The specific surface area is generally 1 to 2500 $gm^{-2}$, and preferably 10 to 1000 $gm^{-2}$. The average particle size and others can be changed by the conditions for preparing the support. The numerical values of these can be selected as appropriate, whereby the reactivity such as the conversion ratio of the alkane and the selectivity for aldehyde, and the reactivity of the substrate for the catalyst can be selected.

A support may be produced and used as the support (B), or a commercially available product may also be used.

(Method for Producing Supported Catalyst (C))

The method for producing the supported catalyst (C) is not particularly limited. For example, the supported catalyst (C) can be obtained by allowing respective compounds of the two metals selected from metals of groups 8 to 10 of the periodic table to be carried on the support (B) and allowing the respective compounds of two metals to react into the bimetallic oxide (A) including oxygen and two metals selected from metals of groups 8 to 10 of the periodic table through a process such as reduction, oxidation, or firing.

For carrying the compounds of metals selected from metals of groups 8 to 10 of the periodic table on the support (B), the respective compounds of two metals selected from metals of groups 8 to 10 of the periodic table may be allowed to be carried sequentially or simultaneously.

Examples of the compound of the metal selected from metals of groups 8 to 10 of the periodic table include a chloride and a complex salt. These are not particularly limited as long as they are ionized in a solvent such as water, and examples thereof include $RuCl_3$, $Pd(NH_3)_2(NO_2)_2$, $IrCl_3$, and $Pt(NH_3)_2 (NO_2)_2$.

For example, the method for producing the supported catalyst includes the following steps:

step (a) impregnating a support with a solution containing a dissolved salt or complex salt of the first metal selected from metals of groups 8 to 10 of the periodic table;

step (b) drying the resulting support and subjecting the dried product to reduction with, for example, $NaBH_4$;

step (c) impregnating the resulting support from the step (b) with a solution containing a dissolved salt or complex salt of a metal different from the first metal (the second metal) selected from metals of groups 8 to 10 of the periodic table.

In the preparing method including steps (a) to (c), the order of the impregnating of the support with the first metal and with the second metal is not particularly limited. After drying, the dried product may be subjected to oxidation in air, or may be fired, if necessary.

Galvanic displacement method can be used for the synthesis of the bimetallic oxide. When this method is used, a bimetallic oxide carried on a support can be obtained by impregnating a support with an electrolytic solution of a metal having a low reduction potential, drying the resulting support, subjecting the resultant to reduction with a reductant, drying again, then further impregnating the resultant with an electrolytic solution of a metal having a high reduction potential, allowing the metals to react with each other to form complex clusters, and then subjecting the resultant to oxidation in air. For example, in a case where a bimetallic oxide of Pd and Ru is obtained, a $Ru^{3+}$ solution is used as the electrolytic solution of a metal having a low reduction potential, a $Pd^{2+}$ solution is used as the electrolytic solution of a metal having a high reduction potential, and $NaBH^4$ is used as the reductant, for example. $Ru^{3+}$ is converted into $Ru^0$ by the reduction reaction; however a reaction: $Pd^{2+}+Ru^0->Pd^0+Ru^{3+}$ is caused, and then a cluster is formed to provide a complex.

(Oxidizer)

The partial oxidation of the alkane is performed in the presence of an oxidizer.

The oxidizer is preferably at least one oxidizer selected from oxygen, nitrogen monoxide, and nitrogen dioxide.

As long as the oxidizer is the above-described compound at the time of the reaction, the oxidizer may be another compound when fed into the reaction system. Examples, which will described later, include examples in which oxygen and nitrogen monoxide are fed; however, for oxygen and nitrogen monoxide, there is an equilibrium reaction between oxygen plus nitrogen monoxide, and nitrogen dioxide, and accordingly, it is considered that there are oxygen, nitrogen monoxide, and nitrogen dioxide at the time of the reaction.

Among these, the combination use of oxygen and nitrogen monoxide as the oxidizer achieves a high selectivity for an aldehyde, particularly when zeolite is used as the support.

In the present invention, the present inventors consider that the aldehyde is produced by the following mechanism: first, the alkane is oxidized by the bimetallic oxide represented by $A_mB_nO_x$ to produce an alcohol; the alcohol is captured by the support due to the interaction between the hydrogen atom of the hydroxyl group of the alcohol and the oxygen of, for example, alumina included in the support; and the alcohol in that state is dehydrogenated to produce an aldehyde. In the present invention, the production of alcohols are not confirmed. The oxidation of the alkane to an alcohol is performed by the catalyst, and the present inventors consider that the reaction proceeds at a low temperature due to this bimetallic oxide.

(Solid Acid (D))

In one preferable embodiment, the partial oxidation of the alkane is performed in the presence of a solid acid (D).

As the solid acid (D), the inorganic oxide described above for the support (B) can be used. Specifically, as the inorganic element used for the inorganic oxide support, those of groups 1 to 4 and 13 to 15 of the periodic table can be used. In the structure of the inorganic oxide, it is preferable that the structure X—O—X is included, wherein X is the element selected.

Furthermore, the inorganic oxide used as the solid acid (D) preferably has an acidity. A factor of having the acidity is the presence of a Bronsted acid site and a Lewis acid site. The acidity of the solid acid (D) varies according to the number of Bronsted acid sites, the number of Lewis acid sites, and the ratio between them. The acidities of solid acids even having the same composition are different from each other due to the structures of the solid acids, and the acidity can be regulated by the conditions for firing and others in the preparation method. The catalytic activity also varies according to the strength of the acidity of the solid acid (D) and the distribution thereof, and the acidity of the support used for the supported catalyst (C). The strength of the acidity of the solid acid (D) is measured by a known method such as an indicator method.

In the present invention, the solid acid (D) is preferably zeolite, $Al_2O_3$, or $ZrO_2$.

As zeolite, the zeolite listed for the support (B) above can be used. A solid acid may be produced and used as the solid acid (D), or a commercially available product of a solid acid may also be used.

As the solid acid (D), a support generally having an average particle size of 1 to 1000 μm, and preferably 10 to 500 μm, can be used. The pore size varies depending on what part of the pore is observed, so that care should be taken therefor, and the maximum size is generally 1 to 1000 nm, and preferably 10 to 500 nm. The specific surface area is generally 1 to 2500 $gm^{-2}$, and preferably 10 to 1000 $gm^{-2}$. The average particle size and others can be changed by the conditions for preparing the support. The numerical values of these can be selected as appropriate, whereby the reactivity such as the conversion ratio of the alkane and the selectivity for aldehyde, and the reactivity of the substrate for the catalyst can be selected.

When the solid acid (D) is used, the amount of the solid acid (D) is preferably 5 to 60 mass %, more preferably 5 to 55 mass %, and even more preferably 10 to 30 mass %, with respect to 100 mass % in total of the supported catalyst (C) and the solid acid (D).

When the partial oxidation is performed in the presence of the solid acid (D), the supported catalyst (C) and the solid acid (D) may be separately present in the reaction system, but generally, a hybrid catalyst (E) described below is preferably used.

(Hybrid Catalyst (E))

The hybrid catalyst (E) is a mixed catalyst obtained by physically mixing the supported catalyst (C) and the solid acid (D). Alternatively, the bimetallic oxide (A) including oxygen and two metals selected from metals of groups 8 to 10 of the periodic table can be carried on a mixture of the support (B) and the solid acid (D) and the resulting product can be used as the hybrid catalyst (E). For cases of using any hybrid catalyst (E), which includes a solid acid, it is considered that oxidative dehydrogenation of methanol as an intermediate is caused on the solid acid, and thus the reaction easily proceeds toward the generation of the aldehyde.

The conversion ratio of the alkane can be increased by using the hybrid catalyst (E). Furthermore, using the combination as described below allows the conversion ratio to further increase. For example, the following is preferred:

the support (B) of the supported catalyst (C) is at least one selected from $Al_2O_3$, $TiO_2$, $ZrO_2$, $CeO_2$, $SiO_2$, and $SiO_2$—$Al_2O_3$, and the solid acid (D) is at least one selected from ZMS-5 zeolite and USY zeolite; or the support (B) of the supported catalyst (C) is ZMS-5 zeolite, and the solid acid (D) is at least one of $Al_2O_3$ or $ZrO_2$.

Also for the hybrid catalyst (E), the total amount of the support (B) and the bimetallic oxide (A) corresponds to the weight of the supported catalyst (C).

Regarding the method for producing the hybrid catalyst (E), physically mixing the supported catalyst (C) and the solid acid (D) allows the hybrid catalyst (E) to be obtained, for example. Particularly, the method preferably includes the following steps:

step (a) mixing predetermined amounts of the two and then grinding the mixture;

step (b) pelletizing the product from step (a); and step (c) pulverizing the product from step (b).

The step (a) may be replaced with the step of allowing the bimetallic oxide (A) to be carried on a hybrid support prepared by physically mixing the powders of the solid acid (D) and the support (B).

In the hybrid catalyst (E) produced through the above-described steps, a fraction having a size of 25 to 45 mesh is preferably used.

(Method for Partial Oxidation)

In the present invention, an alkane is contacted with the above-described supported catalyst (C) in the presence of the oxidizer to convert at least part of the alkane into an aldehyde.

The reaction temperature for partially oxidizing the alkane is preferably 235° C. or more and 350° C. or less, more preferably 260° C. or more and 340° C. or less, and particularly preferably 260° C. or more and 320° C. or less. The pressure when performing the partial oxidation is not particularly limited, and preferably 1 to 10 atm (0.101 to 1.01 MPa), more preferably 1 to 8 atm (0.101 to 0.808 MPa), even more preferably 1 to 5 atm (0.101 to 0.505 MPa), and particularly preferably 1 to 3 atm (0.101 to 0.303 MPa).

In the present invention, the present inventors consider that the reason for the occurrence of the partial oxidation of the alkane is probably that the oxygen atom in the structure A-O-B, wherein A and B mean A and B in the formula (1), in the bimetallic oxide (A) functions as the oxygen source when the alkane is partially oxidized into an aldehyde. When an experiment of temperature programmed desorption of oxygen ($O_2$-TPD) was performed on $Pd_{0.6}Ru_{0.6}O_{1.8}/Al_2O_3$, which is one of the supported catalyst (C) used for the present invention, the desorption of $O_2$ was observed at about 250 to 500° C. Specifically, the result of this experiment suggested that $Pd_{0.6}Ru_{0.6}O_{1.8}/Al_2O_3$ desorbs oxygen at about 250° C., which is a lower temperature than a temperature for conventional partial oxidation of an alkane, and thus the supported catalyst (C) can serve as an oxygen source.

In the present invention, the supported catalyst (C) may be represented by, for example, $Pd_{0.6}Ru_{0.6}O_{1.8}/Al_2O_3$. In this context, the right side of "/", specifically, $Al_2O_3$ in the above example, indicates the substance used as the support (B). The left side of "/", specifically, $Pd_{0.6}Ru_{0.6}O_{1.5}$ in the above example, corresponds to $A_mB_nO_x$ (formula (1)) mentioned above. Accordingly, the recitation "$Pd_{0.6}Ru_{0.6}O_{1.8}/Al_2O_3$" means the following: the support (B) is $Al_2O_3$ in the supported catalyst (C); in the formula (1), Pd and Ru are used as A and B, respectively, and the amounts of Pd, Ru, and oxygen are 0.6 [mmol/g-cat], 0.6 [mmol/g-cat], and 1.8 [mmol/g-cat], respectively.

The partial oxidation may be performed in a batchwise or continuous manner, and a continuous manner is preferable in view of precise control of the partial pressure and the retention time, and improvement in the yield of the aldehyde.

Generally, in the case where the partial oxidation is performed in a continuous manner, the catalyst (the supported catalyst (C) or the hybrid catalyst (E)) is placed in a reaction system, and the alkane and the oxidizer are fed thereinto, whereby the alkane is partially oxidized to convert into an aldehyde. When the alkane and the oxidizer are fed, a gas other than the alkane or the oxidizer may be fed for the purpose of heat removal. Examples of the gas other than the alkane or the oxidizer include helium, carbon dioxide, water vapor, and nitrogen, and helium, carbon dioxide, and water vapor are preferable.

When the partial oxidation is performed, the molar ratio between the alkane and the oxidizer is preferably 20:1 to 1:1.2, and more preferably 15:1 to 1:1.

In the case where oxygen and nitrogen monoxide are used as the oxidizer fed, the molar ratio between them is preferably 1:0.5 to 1:5, and more preferably 1:1 to 1:3.

In the case where the gas other than the alkane or the oxidizer is used in the partial oxidation, the amount of the gas other than the alkane or the oxidizer is preferably 50 to 95 vol %, and more preferably 60 to 90 vol %, with respect to the 100 vol % of the total gas fed.

In the case where the reaction is performed in a flowing manner, the flow rate of the total gas fed is preferably 100 to 300 ml/min, and more preferably 150 to 250 ml/min, per 1 g of the weight of the catalyst.

In the case where the reaction is performed in a batchwise manner, the amount of the total gas is preferably 500 to 3000 ml, and more preferably 1000 to 2000 ml, per 1 g of the weight of the catalyst.

The method of the present invention for partially oxidizing an alkane may also include an optional step as described below. In the present invention, such a step is also referred to as the other step.

For example, the other step may be a separation step of separating the reaction mixture (produced gas) into components after the partial oxidation.

In conventional methods for producing an aldehyde from an alkane, the selectivity is low and a large amount of $CO_2$ is produced as a byproduct. $CO_2$ is difficult to use as, for example, a starting material for a chemical product, and also is one of greenhouse gases. Accordingly, the conventional methods for producing an aldehyde from an alkane have been difficult to put in practical use. On the other hand, in the method of the present invention for partial oxidation, an aldehyde is obtainable from an alkane with a high selectivity. The method of the present invention can also be designed as a single step process at a low temperature and a normal pressure, and is thus applicable to, for example, a distributed small-scale facility that generates methane, such as a livestock farm and residues from bio-ethanol fermentation, to which are conventionally difficult to apply. Accordingly, the method of the present invention enables relative reduction in the amount of $CO_2$ produced, compared to the conventional methods, and is an advantageous method for producing an aldehyde from an alkane.

Examples

Next, the present invention will be further described in detail by way of Experimental Examples, but the present invention is not limited by them.

(Preparation of Reactant Gas)

In Experimental Examples below, an apparatus shown in FIG. 1 was used, and the gas for reaction was produced in the following manner. In the present experimental system, methane was used as an alkane, helium was used as a carrier gas, and oxygen or oxygen/nitrogen monoxide was used as an oxidizer. A reactant gas was prepared using cylinders of the respective compositions as shown in FIG. 1. The reaction was performed at 0.1 MPa. In Experimental Examples described later, pretreatment was performed after oxygen was flowed at 350° C. for 30 minutes. After oxygen was flowed, the pretreatment was performed with the gas as described in Experimental Example, and then the temperature was decreased. When the temperature reached the reaction temperature (300° C.), the reaction was started, and the produced gas was analyzed 1 hour after the start of the reaction.

(Fixed-Bed Flow Reaction System)

In Experimental Examples below, the partial oxidation was performed to convert methane into formaldehyde using the fixed-bed flow reaction system shown in FIG. 1.

A quartz glass tube having an inner diameter of 9 mm and the whole length of 450 mm was used as a reactor. An electric furnace, not shown, was provided to surround the reactor so that it was possible to regulate the temperature. In the reactor, a catalyst layer was formed from any one of the catalysts according to Examples and Comparative examples.

The temperature of the electric furnace was measured with a thermocouple inserted into the center portion of the furnace, and the temperature of the catalyst layer was measured with a thermocouple inserted into the reactor tube. The gas flow rate was regulated with a mass flow controller (MFC) (not shown).

(Analysis of Produced Gas)

In Experimental Examples below, the produced gas after the reaction was analyzed using the fixed-bed flow reaction system shown in FIG. 1.

The produced gas obtained from the outlet of the reactor was analyzed using online GC-TCD and GC-FID (GC-4000plus, manufactured by GL Science Inc.) equipped with a methanizer. The column used was Gaskuropack 54 with a length of 2 m, the detection temperature was 200° C., and the temperature of the methanizer was 350° C.

(X-Ray Crystal Diffractometry)

Analysis by X-ray crystal diffractometry was performed for $Pd_{0.4}Ru_{0.4}O_{1.2}/Al_2O_3$, $Pd_{0.3}Ru_{0.3}O_{0.9}/Al_2O_3$, PdO, Pd, $RuO_2$, and $\eta\text{-}Al_2O_3$.

As $Pd_{0.4}Ru_{0.4}O_{1.2}/Al_2O_3$ and $Pd_{0.3}Ru_{0.3}O_{0.9}/Al_2O_3$, those prepared in Production Examples described later were used for the analysis.

For PdO, Pd, $RuO_2$, and $\eta\text{-}Al_2O_3$, standard spectra were used for the analysis.

The measurement was performed in the following conditions.

Apparatus: RIGAKU (manufactured by Rigaku Corporation)

Measurement conditions: 40 kV, 80 mA, measured from 5° to 80°

Step 0.02°, scan rate (speed) 2° $min^{-1}$

Results are shown in FIG. 2. It was confirmed by the X-ray crystal diffractometry that Pd and Ru in $Pd_{0.4}Ru_{0.4}O_{1.2}/Al_2O_3$ and $Pd_{0.3}Ru_{0.3}O_{0.9}/Al_2O_3$ were present in an oxide state.

($O_2$-TPD)

The behavior of active oxygen was analyzed through Temperature Programmed Desorption (TPD) by the following method for $Pd_{0.3}Ru_{0.3}O_{0.9}/Al_2O_3$, $Pd_{0.4}Ru_{0.4}O_{1.2}/$ $Al_2O_3$, $Pd_{0.5}Ru_{0.5}O_{1.5}/Al_2O_3$, $Pd_{0.6}Ru_{0.6}O_{1.8}/Al_2O_3$, $Pd_{0.7}Ru_{0.7}O_{2.1}/Al_2O_3$, $Pd_{0.6}O_{0.6}/Al_2O_3$, $Ru_{0.6}O_{1.2}/Al_2O_3$, and $Al_2O_3$.

0.5 g of any one of the above described substances as a catalyst was filled in the sample cell of an evaluation apparatus for catalysts (BELCAT II-RSP). 20% $O2/He$ gas was flowed at a flow rate of 50 ml/min, and the temperature was increased from room temperature to 350° C. over 1 hour. The temperature was kept at 350° C. for 30 minutes, and then was decreased to 50° C. At 50° C., the gas was changed to He gas, which was flowed at a flow rate of 50 ml/min for 30 minutes. Then, the temperature was increased from 50° C. 750° C. at a temperature increase rate of 5° C./min, and $O_2$-TPD was measured from the mass signal of m/e=32.

The measurement results of $O_2$-TPD of $Pd_{0.6}Ru_{0.6}O_{1.8}/Al_2O_3$, $Pd_{0.6}O_{0.6}/Al_2O_3$, and $Ru_{0.6}O_{1.2}/Al_2O_3$ are shown in FIG. 3.

The following are shown in FIG. 3. In $Pd_{0.6}O_{0.6}/Al_2O_3$, desorption of oxygen started at 400° C., the desorbing rate became the maximum at 530° C., and the desorption of oxygen was completed at 570° C. On the other hand, in $Pd_{0.6}O_{1.2}/Al_2O_3$, almost no desorption of oxygen was observed at any temperature. On contrary, in $Pd_{0.6}Ru_{0.6}O_{1.8}/Al_2O_3$, desorption of oxygen started in a relatively low temperature range, specifically, at about 250° C., and there was a peak of the desorption of oxygen at about 400 to 450° C. The inventors consider that in $Pd_{0.6}Ru_{0.6}O_{1.8}/Al_2O_3$, Pd and Ru are not present in the form of the respective metal oxides (PdO and $RuO_2$) but in the form of a bimetallic oxide, and that the desorption of oxygen occurs at lower temperature due to the effect exhibited owing to being carried on the support, which contribute to the reaction in the present invention.

The measurement results of $O_2$-TPD of $Pd_{0.3}Ru_{0.3}O_{0.9}/Al_2O_3$, $Pd_{0.4}Ru_{0.4}O_{1.2}/Al_2O_3$, $Pd_{0.5}Ru_{0.5}O_{1.5}/Al_2O_3$, $Pd_{0.6}Ru_{0.6}O_{1.8}/Al_2O_3$, $Pd_{0.7}Ru_{0.7}O_{2.1}/Al_2O_3$, and $Al_2O_3$ are shown in FIG. 4.

The following is shown in FIG. 4. Although the temperature range of the desorption of oxygen shows a similar tendency as in the case shown in FIG. 3, it was found that the peak indicating the desorption of oxygen species was higher as the amount of the bimetallic oxide (A) in the supported catalyst (C) was increased (as m, n, and x in the formula (1) was increased). The height of the peak of the desorption was larger as the amount of the bimetallic oxide (A) in the supported catalyst (C) was increased. On the other hand, almost no desorption of oxygen was observed in $Al_2O_3$ as a support. The present inventors consider from these that desorbed oxygen is oxygen derived from Pd— O—Ru carried on the support.

(Production of Supported Catalyst and Hybrid Catalyst)

Production Example 1

A support ZSM-5(50) (available from ZEOLYST) was fired at 500° C. for 13 hours. 4.59 g of the fired support was impregnated with an aqueous solution containing 0.52 g (2.0 mmol) of $RuCl_3\cdot3H_2O$, and the resultant was then dried at 120° C. for 12 hours to obtain $RuCl_3/ZSM\text{-}5(50)$. After drying, $RuCl_3/ZSM\text{-}5(50)$ was impregnated with an aqueous solution containing $NaBH_4$ (0.23 g: 6.1 mmol) (the amount of $NaBH_4$ necessary for the reduction of $Ru^{2+}$) to react with each other to reduce the metal carried, and the resultant was then dried at 120° C. for 12 hours to obtain Ru/ZSM-5(50).

To Ru/ZSM-5(50), 4.3 ml of a $Pd(NH_3)_2(NO_2)_2$ aqueous solution (469.8 mmol/L) was added, so that Ru/ZSM-5(50) was immersed therewith, and the resultant was then dried at 120° C. for 12 hours.

The solid obtained was heated to 350° C. in air in a furnace over 2 hours to cause decomposition, and then further fired at 350° C. for 0.5 hours to obtain 5 g of $Pd_{0.4}Ru_{0.4}O_{1.2}$/ZSM-5(50).

Production Example 2

$Pd_{0.5}Ru_{0.5}O_{1.5}$/ZSM-5(50) was obtained in the same manner as in Production Example 1, except that the amounts of the reagents in Production Example 1 were adjusted.

Production Example 3

$Pd_{0.6}Ru_{0.6}O_{1.8}$/ZSM-5(50) was obtained in the same manner as in Production Example 1, except that the amounts of the reagents in Production Example 1 were adjusted.

Production Example 4

$Pd_{0.4}Ru_{0.4}O_{1.2}$/ZSM-5(50) obtained in Production Example 1 and $Al_2O_3$ (available from Kojundo Chemical Lab. Co., Ltd., η-$Al_2O_3$) that had been fired at 500° C. for 2 hours were physically mixed in a mass ratio of 80:20, and the mixture was shaped into granules, which were regulated to 25 to 45 mesh, to thereby obtain 80% $Pd_{0.4}Ru_{0.4}O_{1.2}$/ZSM-5(50)+20% $Al_2O_3$(hybrid catalyst).

Production Example 5

A support ZSM-5(50) (available from ZEOLYST) was fired at 500° C. for 2 hours. 4.79 g of the fired support was impregnated with 4.3 ml of a $Pd(NH_3)_2(NO_2)_2$ aqueous solution (469.8 mmol/L), and the resultant was then dried at 120° C. for 12 hours. After drying, the resultant was impregnated with an aqueous solution containing $NaBH_4$ (0.15 g: 4 mmol) to cause a reaction to reduce the metal carried, and the resultant was dried at 120° C. for 12 hours. The solid obtained was heated to 350° C. in air in a furnace over 2 hours to cause decomposition, and then further fired at 350° C. for 0.5 hours to obtain $Pd_{0.4}O_{0.4}$/ZSM-5(50).

Production Example 6

The fired support was impregnated with an aqueous solution containing 0.52 g (2.0 mmol) of $RuCl_3 \cdot 3H_2O$ instead of the $Pd(NH_3)_2(NO_2)_2$ aqueous solution in Production Example 5, and the resultant was then dried at 120° C. for 12 hours. After drying, the resultant was impregnated with an aqueous solution containing $NaBH_4$ (0.23 g: 6.1 mmol) to cause a reaction to reduce the metal carried, and the resultant was dried at 120° C. for 12 hours. The solid obtained was heated to 350° C. in air in a furnace over 2 hours to cause decomposition, and then further fired at 350° C. for 0.5 hours to obtain $Ru_{0.4}O_{0.8}$/ZSM-5(50).

Production Example 7

$Pd_{0.4}Ru_{0.4}O_{1.2}$/USY(30) was obtained in the same manner as in Production Example 1, except that USY(30) (available from JGC Catalysts and Chemicals Ltd.) was used instead of the support ZSM-5(50) (available from ZEOLYST) in Production Example 1, and that the amounts of reagents were adjusted.

Production Example 8

$Pd_{0.2}Ru_{0.2}O_{0.6}$/$SiO_2$ was obtained in the same manner as in Production Example 1, except that $SiO_2$ (available from FUJISILYSIA CHEMICAL LTD.) was used instead of the support ZSM-5(50) (available from ZEOLYST) in Production Example 1, and that the amounts of reagents were adjusted.

Production Example 9

$Pd_{0.3}Ru_{0.3}O_{0.9}$/$Al_2O_3$ was obtained in the same manner as in Production Example 1, except that $Al_2O_3$ (available from Kojundo Chemical Lab. Co., Ltd., η-$Al_2O_3$) was used instead of the support ZSM-5(50) (available from ZEOLYST) in Production Example 1, and that the amounts of reagents were adjusted.

Production Example 10

$Pd_{0.4}Ru_{0.4}O_{1.2}$/$Al_2O_3$ was obtained in the same manner as in Production Example 9, except that the amounts of the reagents in Production Example 9 were adjusted.

Production Example 11

$Pd_{0.5}Ru_{0.5}O_{1.5}$/$Al_2O_3$ was obtained in the same manner as in Production Example 9, except that the amounts of the reagents in Production Example 9 were adjusted.

Production Example 12

$Pd_{0.6}Ru_{0.6}O_{1.8}$/$Al_2O_3$ was obtained in the same manner as in Production Example 9, except that the amounts of the reagents in Production Example 9 were adjusted.

Production Example 13

$Pd_{0.7}Ru_{0.7}O_{2.1}$/$Al_2O_3$ was obtained in the same manner as in Production Example 9, except that the amounts of the reagents in Production Example 9 were adjusted.

Production Example 14

$Pd_{0.3}Ru_{0.3}O_{0.9}$/$TiO_2$ was obtained in the same manner as in Production Example 1, except that $TiO_2$ (available from KANTO CHEMICAL CO., INC.) was used instead of the support ZSM-5(50) (available from ZEOLYST) in Production Example 1, and that the amounts of reagents were adjusted.

Production Example 15

$Pd_{0.3}Ru_{0.3}O_{0.9}$/$CeO_2$ was obtained in the same manner as in Production Example 1, except that $CeO_2$ (available from KANTO CHEMICAL CO., INC.) was used instead of the support ZSM-5(50) (available from ZEOLYST) in Production Example 1, and that the amounts of reagents were adjusted.

Production Example 16

$Pd_{0.3}Ru_{0.3}O_{0.9}$/$ZrO_2$ was obtained in the same manner as in Production Example 1, except that $ZrO_2$ (available from KANTO CHEMICAL CO., INC.) was used instead of the support ZSM-5(50) (available from ZEOLYST) in Production Example 1, and that the amounts of reagents were adjusted.

Production Example 17

$Pd_{0.3}Ru_{0.3}O_{0.9}/SiO_2$-$Al_2O_3$ was obtained in the same manner as in Production Example 1, except that $SiO_2$—$Al_2O_3$ (available from FUJISILYSIA CHEMICAL LTD) was used instead of the support ZSM-5(50) (available from ZEOLYST) in Production Example 1, and that the amounts of reagents were adjusted.

Production Example 18

$Ir_{0.4}Ru_{0.4}O_{1.6}/Al_2O_3$ was obtained in the same manner as in Production Example 1, except that $Al_2O_3$ (available from Kojundo Chemical Lab. Co., Ltd., $\eta$-$Al_2O_3$) and an $IrCl_3$ aqueous solution were used instead of the support ZSM-5 (50) (available from ZEOLYST) and the $Pd(NH_3)_2(NO_2)_2$ aqueous solution, respectively, in Production Example 1, and that the amounts of reagents were adjusted.

Production Example 19

$Pd_{0.4}Ir_{0.4}O_{1.2}/Al_2O_3$ was obtained in the same manner as in Production Example 1, except that $Al_2O_3$ (available from Kojundo Chemical Lab. Co., Ltd., $\eta$-$Al_2O_3$) and an $IrCl_3$ aqueous solution were used instead of the support ZSM-5 (50) (available from ZEOLYST) and the $RuCl_3 \cdot 3H_2O$ aqueous solution, respectively, in Production Example 1, and that the amounts of reagents were adjusted.

Production Example 20

$Pt_{0.1}Ru_{0.1}O_{0.3}/Al_2O_3$ was obtained in the same manner as in Production Example 1, except that $Al_2O_3$ (available from Kojundo Chemical Lab. Co., Ltd., $\eta$-$Al_2O_3$) and a $Pt(NH_3)_2(NO_2)_2$ aqueous solution were used instead of the support ZSM-5(50) (available from ZEOLYST) and the $Pd(NH_3)_2(NO_2)_2$ aqueous solution, respectively, in Production Example 1, and that the amounts of reagents were adjusted.

Production Example 21

$Pt_{0.2}Ir_{0.2}O_{0.6}/Al_2O_3$ was obtained in the same manner as in Production Example 1, except that $Al_2O_3$ (available from Kojundo Chemical Lab. Co., Ltd., $\eta$-$Al_2O_3$), a $Pt(NH_3)_2(NO_2)_2$ aqueous solution, and $IrCl_3$ aqueous solution were used instead of the support ZSM-5(50) (available from ZEOLYST), the $Pd(NH_3)_2(NO_2)_2$ aqueous solution, and the $RuCl_3 \cdot 3H_2O$ aqueous solution, respectively, in Production Example 1, and that the amounts of reagents were adjusted.

Production Example 22

$Pd_{0.1}Ru_{0.3}O_{0.7}/Al_2O_3$ was obtained in the same manner as in Production Example 9, except that the amounts of the reagents in Production Example 9 were adjusted.

Production Example 23

$Pd_{0.4}Ru_{0.4}O_{1.2}/((38)$ was obtained in the same manner as in Production Example 1, except that beta zeolite(38) (also referred to as B(38)) (available from ZEOLYST) was used instead of the support ZSM-5(50) (available from ZEOLYST) in Production Example 1, and that the amounts of reagents were adjusted.

Production Example 24

$Pd_{0.3}Ru_{0.3}O_{0.9}/ZSM$-5(50) was obtained in the same manner as in Production Example 1, except that the amounts of the reagents in Production Example 1 were adjusted.

Production Example 25

$Pd_{0.4}Ru_{0.4}O_{1.2}/ZSM$-5(50) obtained in Production Example 1 and $ZrO_2$ (available from KANTO CHEMICAL CO., INC.) that had been fired at 500° C. for 2 hours were physically mixed in a mass ratio of 80:20, and the mixture was shaped into granules, which were regulated to 25 to 45 mesh, to thereby obtain 80% $Pd_{0.4}Ru_{0.4}O_{1.2}/ZSM$-5(50)+ 20% $ZrO_2$ (hybrid catalyst).

Production Example 26

$Pd_{0.4}Ru_{0.4}O_{1.2}/ZSM$-5(50) obtained in Production Example 1 and $ZrO_2$ (available from KANTO CHEMICAL CO., INC.) that had been fired at 500° C. for 2 hours were physically mixed in a mass ratio of 60:40, and the mixture was shaped into granules, which were regulated to 25 to 45 mesh, to thereby obtain 60% $Pd_{0.4}Ru_{0.4}O_{1.2}/ZSM$-5(50)+ 40% $ZrO_2$ (hybrid catalyst).

Production Example 27

$Pd_{0.4}Ru_{0.4}O_{1.2}/Al_2O_3$ obtained in Production Example 10 and ZSM-5(50) (available from ZEOLYST) that had been fired at 500° C. for 2 hours were physically mixed in a mass ratio of 95:5, and the mixture was shaped into granules, which were regulated to 25 to 45 mesh, to thereby obtain 95% $Pd_{0.4}Ru_{0.4}O_{1.2}/Al_2O_3$+5% ZSM-5(50) (hybrid catalyst).

Production Example 28

$Pd_{0.4}Ru_{0.4}O_{1.2}/Al_2O_3$ obtained in Production Example 10 and ZSM-5(50) (available from ZEOLYST) that had been fired at 500° C. for 2 hours were physically mixed in a mass ratio of 70:30, and the mixture was shaped into granules, which were regulated to 25 to 45 mesh, to thereby obtain 70% $Pd_{0.4}Ru_{0.4}O_{1.2}/Al_2O_3$+30% ZSM-5(50) (hybrid catalyst).

Production Example 29

$Pd_{0.3}Ru_{0.3}O_{0.9}/Al_2O_3$ obtained in Production Example 9 and ZSM-5(50) (available from ZEOLYST) that had been fired at 500° C. for 2 hours were physically mixed in a mass ratio of 90:10, and the mixture was shaped into granules, which were regulated to 25 to 45 mesh, to thereby obtain 90% $Pd_{0.3}Ru_{0.3}O_{0.9}/Al_2O_3$+10% ZSM-5(50) (hybrid catalyst).

Production Example 30

$Pd_{0.3}Ru_{0.3}O_{0.9}/TiO_2$ obtained in Production Example 14 and ZSM-5(50) (available from ZEOLYST) that had been fired at 500° C. for 2 hours were physically mixed in a mass ratio of 95:5, and the mixture was shaped into granules, which were regulated to 25 to 45 mesh, to thereby obtain 95% $Pd_{0.3}Ru_{0.3}O_{0.9}/TiO_2$+5% ZSM-5(50) (hybrid catalyst).

Production Example 31

$Pd_{0.3}Ru_{0.3}O_{0.9}/TiO_2$ obtained in Production Example 14 and ZSM-5(50) (available from ZEOLYST) that had been fired at 500° C. for 2 hours were physically mixed in a mass ratio of 90:10, and the mixture was shaped into granules, which were regulated to 25 to 45 mesh, to thereby obtain 90% $Pd_{0.3}Ru_{0.3}O_{0.9}/TiO_2$+10% ZSM-5(50) (hybrid catalyst).

Production Example 32

$Pd_{0.3}Ru_{0.3}O_{0.9}/SiO_2$—$Al_2O_3$ obtained in Production Example 17 and ZSM-5(50) (available from ZEOLYST) that had been fired at 500° C. for 2 hours were physically mixed in a mass ratio of 90:10, and the mixture was shaped into granules, which were regulated to 25 to 45 mesh, to thereby obtain 90% $Pd_{0.3}Ru_{0.3}O_{0.9}/SiO_2$-$Al_2O_3$+10% ZSM-5(50) (hybrid catalyst).

Production Example 33

$Pd_{0.3}Ru_{0.3}O_{0.9}/SiO_2$—$Al_2O_3$ obtained in Production Example 17 and ZSM-5(50) (available from ZEOLYST) that had been fired at 500° C. for 2 hours were physically mixed in a mass ratio of 80:20, and the mixture was shaped into granules, which were regulated to 25 to 45 mesh, to thereby obtain 80% $Pd_{0.3}Ru_{0.3}O_{0.9}/SiO_2$-$Al_2O_3$+20% ZSM-5(50) (hybrid catalyst).

Production Example 34

$Pd_{0.3}Ru_{0.3}O_{0.9}/CeO_2$ obtained in Production Example 15 and ZSM-5(50) (available from ZEOLYST) that had been fired at 500° C. for 2 hours were physically mixed in a mass ratio of 90:10, and the mixture was shaped into granules, which were regulated to 25 to 45 mesh, to thereby obtain 90% $Pd_{0.3}Ru_{0.3}O_{0.9}/CeO_2$+10% ZSM-5(50) (hybrid catalyst).

Production Example 35

$Pd_{0.3}Ru_{0.3}O_{0.9}/CeO_2$ obtained in Production Example 15 and ZSM-5(50) (available from ZEOLYST) that had been fired at 500° C. for 2 hours were physically mixed in a mass ratio of 80:20, and the mixture was shaped into granules, which were regulated to 25 to 45 mesh, to thereby obtain 80% $Pd_{0.3}Ru_{0.3}O_{0.9}/CeO_2$+20% ZSM-5(50) (hybrid catalyst).

Production Example 36

$Pd_{0.3}Ru_{0.3}O_{0.9}/CeO_2$ obtained in Production Example 15 and ZSM-5(50) (available from ZEOLYST) that had been fired at 500° C. for 2 hours were physically mixed in a mass ratio of 70:30, and the mixture was shaped into granules, which were regulated to 25 to 45 mesh, to thereby obtain 70% $Pd_{0.3}Ru_{0.3}O_{0.9}/CeO_2$+30% ZSM-5(50) (hybrid catalyst).

Production Example 37

$Pd_{0.3}Ru_{0.3}O_{0.9}/ZrO_2$ obtained in Production Example 16 and ZSM-5(50) (available from ZEOLYST) that had been fired at 500° C. for 2 hours were physically mixed in a mass ratio of 90:10, and the mixture was shaped into granules, which were regulated to 25 to 45 mesh, to thereby obtain 90% $Pd_{0.3}Ru_{0.3}O_{0.9}/ZrO_2$+10% ZSM-5(50) (hybrid catalyst).

Production Example 38

$Pd_{0.3}Ru_{0.3}O_{0.9}/ZrO_2$ obtained in Production Example 16 and ZSM-5(50) (available from ZEOLYST) that had been fired at 500° C. for 2 hours were physically mixed in a mass ratio of 80:20, and the mixture was shaped into granules, which were regulated to 25 to 45 mesh, to thereby obtain 80% $Pd_{0.3}Ru_{0.3}O_{0.9}/ZrO_2$+20% ZSM-5(50) (hybrid catalyst).

Production Example 39

$Pd_{0.2}Ru_{0.2}O_{0.6}/SiO_2$ obtained in Production Example 8 and ZSM-5(50) (available from ZEOLYST) that had been fired at 500° C. for 2 hours were physically mixed in a mass ratio of 50:50, and the mixture was shaped into granules, which were regulated to 25 to 45 mesh, to thereby obtain 50% $Pd_{0.2}Ru_{0.2}O_{0.6}/SiO_2$+50% ZSM-5(50) (hybrid catalyst).

Production Example 40

$Pd_{0.2}Ru_{0.2}O_{0.6}/SiO_2$ obtained in Production Example 8 and ZSM-5(50) (available from ZEOLYST) that had been fired at 500° C. for 2 hours were physically mixed in a mass ratio of 40:60, and the mixture was shaped into granules, which were regulated to 25 to 45 mesh, to thereby obtain 40% $Pd_{0.2}Ru_{0.2}O_{0.6}/SiO_2$+60% ZSM-5(50) (hybrid catalyst).

Production Example 41

$Pd_{0.4}Ru_{0.4}O_{1.2}/ZSM-5(50)$ obtained in Production Example 1 and ZSM-5(50) (available from ZEOLYST) that had been fired at 500° C. for 2 hours were physically mixed in a mass ratio of 50:50, and the mixture was shaped into granules, which were regulated to 25 to 45 mesh, to thereby obtain 50% $Pd_{0.4}Ru_{0.4}O_{1.2}/ZSM-5(50)$+50% ZSM-5(50) (hybrid catalyst).

Production Example 42

$Pd_{0.4}Ru_{0.4}O_{1.2}/Al_2O_3$ obtained in Production Example 10 and $Al_2O_3$ (available from Kojundo Chemical Lab. Co., Ltd., $\eta$-$Al_2O_3$) that had been fired at 500° C. for 2 hours were physically mixed in a mass ratio of 50:50, and the mixture was shaped into granules, which were regulated to 25 to 45 mesh, to thereby obtain 50% $Pd_{0.4}Ru_{0.4}O_{1.2}/Al_2O_3$+50% $Al_2O_3$(hybrid catalyst).

Production Example 43

$Pd_{0.4}Ru_{0.2}O_{0.8}/Al_2O_3$ was obtained in the same manner as in Production Example 9, except that the amounts of reagents in Production Example 9 were adjusted.

Production Example 44

$Pd_{0.2}Ru_{0.4}O_{1.0}/Al_2O_3$ was obtained in the same manner as in Production Example 9, except that the amounts of reagents in Production Example 9 were adjusted.

Production Example 45

$Pd_{0.6}Ru_{0.6}O_{1.8}/Al_2O_3$ obtained in Production Example 12 and USY(10) (available from available from JGC Catalysts and Chemicals Ltd.) that had been fired at 500° C. for 2 hours were physically mixed in a mass ratio of 90:10, and the mixture was shaped into granules, which were regulated to 25 to 45 mesh, to thereby obtain 90% $Pd_{0.6}Ru_{0.6}O_{1.8}/Al_2O_3$+10% USY(10) (hybrid catalyst).

Production Example 46

$Pd_{0.6}Ru_{0.6}O_{1.8}/Al_2O_3$ obtained in Production Example 12 and $Al_2O_3$ (available from Kojundo Chemical Lab. Co., Ltd., $\eta$-$Al_2O_3$) that had been fired at 500° C. for 2 hours were physically mixed in a mass ratio of 50:50, and the mixture was shaped into granules, which were regulated to 25 to 45 mesh, to thereby obtain 50% $Pd_{0.6}Ru_{0.6}O_{1.8}/Al_2O_3$+50% $Al_2O_3$(hybrid catalyst).

Production Example 47

Catalysts each including the metal oxide (A) and the support (B) and the solid acid (D) in the amounts shown in Tables 12 to 18 were prepared in the same manner as in Production Examples 1 to 46 described above. In some of Experimental Examples and Comparative Examples, $\gamma$-alumina available from Strem Chemicals, Inc. was used as alumina instead of $Al_2O_3$ (available from Kojundo Chemical Lab. Co., Ltd., $\eta$-$Al_2O_3$). For the cases where this alumina was used, it is designated as $\gamma$-$Al_2O_3$. In Examples, $\eta Al_2O_3$ and $\gamma$-$Al_2O_3$ are indicated distinguishably.

Experimental Example A 500 mg of a supported catalyst obtained in any one of Production Examples described above was loaded on the reactor of the above-described fixed-bed flow reaction system. Pretreatment was performed by flowing a gas containing, in helium, 13.4 vol % of methane, 1.7 vol % of nitrogen monoxide, and 0.7 vol % of oxygen at 350° C. for 30 minutes, and then the gas having the same composition was flowed into the fixed-bed flow reaction system at 300° C. to cause a reaction. The flow rate of the gas was 100 ml/min. The composition of the gas produced one hour after the start of the flowing was examined, and the selectivity (%), the conversion ratio (%), and the yield (%) were determined. The results are shown in Table 1.

TABLE 1

| Catalyst | Reaction temperature (° C.) | Conversion ratio (%) | Selectivity (%) | Yield (%) |
|---|---|---|---|---|
| $Ir_{0.4}Ru_{0.4}O_{1.6}/Al_2O_3$ | 300 | 0.22 | 14.00 | 0.031 |
| $Pd_{0.4}Ir_{0.4}O_{1.2}/Al_2O_3$ | 300 | 0.06 | 12.78 | 0.008 |
| $Pt_{0.1}Ru_{0.1}O_{0.3}/Al_2O_3$ | 300 | 0.3 | 20.51 | 0.062 |

TABLE 1-continued

| Catalyst | Reaction temperature (° C.) | Conversion ratio (%) | Selectivity (%) | Yield (%) |
|---|---|---|---|---|
| $Pt_{0.2}Ir_{0.2}O_{0.6}/Al_2O_3$ | 300 | 0.31 | 10.97 | 0.034 |
| $Pd_{0.4}Ru_{0.4}O_{1.2}/Al_2O_3$ | 300 | 0.14 | 40.00 | 0.056 |
| $Pd_{0.1}Ru_{0.3}O_{0.7}/Al_2O_3$ | 300 | 0.06 | 46.00 | 0.028 |

Experimental Example B

The experiment was performed in the same manner as in Experimental Example A, except for changing the supported catalyst to those described in Table 2.

In Table 2, the example in which $Pd_{0.4}O_{0.4}/ZSM$-5(50) was used, the example in which $Ru_{0.4}O_{0.8}/ZSM$-5(50) was used, and the example in which ZSM-5(50), which is not a supported catalyst but a solid acid, was used do not correspond to the present invention but Comparative Examples.

When only ZSM-5(50) was used, the reaction was not caused. When the metal species was only Ru, the conversion ratio was remarkably low, and when the metal species was only Pd, the selectivity was remarkably low.

TABLE 2

| Catalyst | Reaction temperature (° C.) | Conversion ratio (%) | Selectivity (%) | Yield (%) |
|---|---|---|---|---|
| $Pd_{0.4}Ru_{0.4}O_{1.2}/ZSM$-5 (50) | 300 | 0.14 | 62.00 | 0.087 |
| $Ru_{0.4}O_{0.8}/ZSM$-5 (50) | 300 | 0.06 | 15.78 | 0.009 |
| $Pd_{0.4}O_{0.4}/ZSM$-5 (50) | 300 | 0.43 | 0.48 | 0.002 |
| ZSM-5 (50) | 300 | 0.10 | 0.00 | 0.000 |

Experimental Example C

The experiment was performed in the same manner as in Experimental Example A, except for changing the supported catalyst to those described in Table 3.

TABLE 3

| Catalyst | Reaction temperature (° C.) | Conversion ratio (%) | Selectivity (%) | Yield (%) |
|---|---|---|---|---|
| $Pd_{0.4}Ru_{0.4}O_{1.2}/ZSM$-5 (50) | 300 | 0.14 | 62.00 | 0.087 |
| $Pd_{0.4}Ru_{0.4}O_{1.2}/Al_2O_3$ | 300 | 0.10 | 56.24 | 0.056 |
| $Pd_{0.4}Ru_{0.4}O_{1.2}/USY$ (30) | 300 | 0.03 | 43.00 | 0.013 |
| $Pd_{0.4}Ru_{0.4}O_{1.2}/USY$ (30) | 300 | 0.05 | 23.00 | 0.012 |
| $Pd_{0.4}Ru_{0.4}O_{1.2}/\beta$ (38) | 300 | 0.09 | 41.00 | 0.037 |

Experimental Example D

The experiment was performed in the same manner as in Experimental Example A, except for changing the supported catalyst to those described in Table 4.

TABLE 4

| Catalyst | Reaction temperature (° C.) | Conversion ratio (%) | Selectivity (%) | Yield (%) |
|---|---|---|---|---|
| $Pd_{0.3}Ru_{0.3}O_{0.9}/Al_2O_3$ | 300 | 0.08 | 60.00 | 0.048 |

TABLE 4-continued

| Catalyst | Reaction temperature (° C.) | Conversion ratio (%) | Selectivity (%) | Yield (%) |
|---|---|---|---|---|
| $Pd_{0.3}Ru_{0.3}O_{0.9}/TiO_2$ | 300 | 0.05 | 42.00 | 0.021 |
| $Pd_{0.3}Ru_{0.3}O_{0.9}/SiO_2$—$Al_2O_3$ | 300 | 0.06 | 51.00 | 0.031 | catalyst to a supported catalyst or a hybrid catalyst described in Table 6 or 7. Also in cases where a hybrid catalyst was used, the amount of the catalyst was 500 mg in total.

In Tables, % means the weight ratio of the supported catalyst (C) and that of the solid acid (D) to the total 100 wt % of the supported catalyst (C) and the solid acid (D).

In some examples described in Table 7, not only the catalyst but also the reaction temperature were changed.

TABLE 6

| Catalyst | Reaction temperature (° C.) | Conversion ratio (%) | Selectivity (%) | Yield (%) |
|---|---|---|---|---|
| $Pd_{0.4}Ru_{0.4}O_{1.2}/ZSM$-5 (50) | 300 | 0.14 | 62.00 | 0.087 |
| 80% $Pd_{0.4}Ru_{0.4}O_{1.2}/ZSM$-5 (50) + 20% $Al_2O_3$ | 300 | 0.12 | 64.64 | 0.078 |
| $Pd_{0.4}Ru_{0.4}O_{1.2}/ZSM$-5 (50) | 300 | 0.14 | 52.00 | 0.073 |
| 80% $Pd_{0.4}Ru_{0.4}O_{1.2}/ZSM$-5 (50) + 20% $ZrO_2$ | 300 | 0.31 | 34.06 | 0.106 |
| 60% $Pd_{0.4}Ru_{0.4}O_{1.2}/ZSM$-5 (50) + 40% $ZrO_2$ | 300 | 0.25 | 33.43 | 0.084 |
| $Pd_{0.4}Ru_{0.4}O_{1.2}/Al_2O_3$ | 300 | 0.10 | 56.24 | 0.056 |
| 95% $Pd_{0.4}Ru_{0.4}O_{1.2}/Al_2O_3$ + 5% ZSM-5 (50) | 300 | 0.11 | 55.26 | 0.061 |
| 70% $Pd_{0.4}Ru_{0.4}O_{1.2}/Al_2O_3$ + 30% ZSM-5 (50) | 300 | 0.12 | 55.00 | 0.066 |
| $Pd_{0.3}Ru_{0.3}O_{0.9}/Al_2O_3$ | 300 | 0.08 | 60.00 | 0.048 |
| 90% $Pd_{0.3}Ru_{0.3}O_{0.9}/Al_2O_3$ + 10% ZSM-5 (50) | 300 | 0.09 | 60.94 | 0.055 |
| $Pd_{0.3}Ru_{0.3}O_{0.9}/TiO_2$ | 300 | 0.05 | 42.00 | 0.021 |
| 95% $Pd_{0.3}Ru_{0.3}O_{0.9}/TiO_2$ + 5% ZSM-5 (50) | 300 | 0.06 | 43.00 | 0.026 |
| 90% $Pd_{0.3}Ru_{0.3}O_{0.9}/TiO_2$ + 10% ZSM-5 (50) | 300 | 0.09 | 43.00 | 0.039 |
| $Pd_{0.3}Ru_{0.3}O_{0.9}/SiO_2$—$Al_2O_3$ | 300 | 0.06 | 51.00 | 0.031 |
| 90% $Pd_{0.3}Ru_{0.3}O_{0.9}/SiO_2$—$Al_2O_3$ + 10% ZSM-5 (50) | 300 | 0.06 | 52.00 | 0.031 |
| 80% $Pd_{0.3}Ru_{0.3}O_{0.9}/SiO_2$—$Al_2O_3$ + 20% ZSM-5 (50) | 300 | 0.07 | 54.00 | 0.038 |

TABLE 4-continued

| Catalyst | Reaction temperature (° C.) | Conversion ratio (%) | Selectivity (%) | Yield (%) |
|---|---|---|---|---|
| $Pd_{0.3}Ru_{0.3}O_{0.9}/ZrO_2$ | 300 | 0.03 | 45.00 | 0.014 |

Experimental Example E

The experiment was performed in the same manner as in Experimental Example A, except for changing the supported catalyst to those described in Table 5.

TABLE 5

| Catalyst | Reaction temperature (° C.) | Conversion ratio (%) | Selectivity (%) | Yield (%) |
|---|---|---|---|---|
| $Pd_{0.4}Ru_{0.4}O_{1.2}/ZSM$-5 (50) | 300 | 0.14 | 62.00 | 0.087 |
| $Pd_{0.6}Ru_{0.6}O_{1.8}/ZSM$-5 (50) | 300 | 0.09 | 59.72 | 0.054 |

Experimental Example F

The experiment was performed in the same manner as in Experimental Example A, except for changing the supported

TABLE 7

| Catalyst | Reaction temperature (° C.) | Conversion ratio (%) | Selectivity (%) | Yield (%) |
|---|---|---|---|---|
| 90% $Pd_{0.3}Ru_{0.3}O_{0.9}/CeO_2$ + 10% ZSM-5 (50) | 300 | 0.03 | 46.00 | 0.014 |
| 80% $Pd_{0.3}Ru_{0.3}O_{0.9}/CeO_2$ + 20% ZSM-5 (50) | 300 | 0.04 | 51.55 | 0.021 |
| 70% $Pd_{0.3}Ru_{0.3}O_{0.9}/CeO_2$ + 30% ZSM-5 (50) | 300 | 0.04 | 54.05 | 0.022 |
| $Pd_{0.3}Ru_{0.3}O_{0.9}/ZrO_2$ | 300 | 0.03 | 45.00 | 0.014 |
| 90% $Pd_{0.3}Ru_{0.3}O_{0.9}/ZrO_2$ + 10% ZSM-5 (50) | 300 | 0.05 | 45.00 | 0.023 |
| 80% $Pd_{0.3}Ru_{0.3}O_{0.9}/ZrO_2$ + 20% ZSM-5 (50) | 300 | 0.06 | 49.00 | 0.029 |
| 50% $Pd_{0.2}Ru_{0.2}O_{0.6}/SiO_2$ + 50% ZSM-5 (50) | 240 | 0.04 | 66.00 | 0.026 |
| 50% $Pd_{0.2}Ru_{0.2}O_{0.6}/SiO_2$ + 50% ZSM-5 (50) | 250 | 0.05 | 60.00 | 0.030 |
| 50% $Pd_{0.2}Ru_{0.2}O_{0.6}/SiO_2$ + 50% ZSM-5 (50) | 260 | 0.06 | 54.00 | 0.032 |

Experimental Example G

The experiment was performed in the same manner as in Experimental Example A, except that the supported catalyst was changed to those described in Table 8, that the same gas as in Experimental Example A (a gas containing, in helium, 13.4 vol % of methane, 1.7 vol % of nitrogen monoxide, and 0.7 vol % of oxygen) was used in the cases where $NO+O_2$ is put in the cell of Oxidizer in Table 8, and that a gas containing, in helium, 13.4 vol % of methane and 0.7 vol % of oxygen was used in the cases where $O_2$ is put in the cell.

TABLE 8

| Catalyst | Reaction temperature (° C.) | Conversion ratio (%) | Selectivity (%) | Yield (%) | Oxidizer |
|---|---|---|---|---|---|
| $Pd_{0.4}Ru_{0.4}O_{1.2}$/ZSM-5 (50) | 300 | 0.14 | 62.00 | 0.087 | $NO + O_2$ |
| $Pd_{0.4}Ru_{0.4}O_{1.2}$/ZSM-5 (50) | 300 | 0.08 | 32.00 | 0.026 | $O_2$ |
| $Pd_{0.4}Ru_{0.4}O_{1.2}$/USY (30) | 300 | 0.03 | 43.00 | 0.013 | $NO + O_2$ |
| $Pd_{0.4}Ru_{0.4}O_{1.2}$/USY (30) | 300 | 0.06 | 22.71 | 0.011 | $O_2$ |
| $Pd_{0.3}Ru_{0.3}O_{0.9}$/$Al_2O_3$ | 300 | 0.08 | 60.00 | 0.048 | $O_2$ |
| $Pd_{0.3}Ru_{0.3}O_{0.9}$/$ZrO_2$ | 300 | 0.03 | 45.00 | 0.014 | $NO + O_2$ |
| $Pd_{0.3}Ru_{0.3}O_{0.9}$/$ZrO_2$ | 300 | 0.04 | 39.00 | 0.016 | $O_2$ |
| $Pd_{0.3}Ru_{0.3}O_{0.9}$/$TiO_2$ | 300 | 0.05 | 42.00 | 0.021 | $NO + O_2$ |
| $Pd_{0.3}Ru_{0.3}O_{0.9}$/$TiO_2$ | 300 | 0.07 | 25.51 | 0.018 | $O_2$ |

Experimental Example H

The experiment was performed in the same manner as in Experimental Example A, except that the supported catalyst was changed to a supported catalyst or a hybrid catalyst described in Table 9, and that the reaction temperature was changed as described in Table 9. Also in cases where a hybrid catalyst was used, the amount of the catalyst was 500 mg in total.

TABLE 9

| Catalyst | Reaction temperature (° C.) | Conversion ratio (%) | Selectivity (%) | Yield (%) |
|---|---|---|---|---|
| $Pd_{0.4}Ru_{0.4}O_{1.2}$/ ZSM-5 (50) | 275 | 0.05 | 72.00 | 0.036 |
| $Pd_{0.4}Ru_{0.4}O_{1.2}$/ ZSM-5 (50) | 280 | 0.06 | 72.15 | 0.043 |
| $Pd_{0.4}Ru_{0.4}O_{1.2}$/ ZSM-5 (50) | 285 | 0.07 | 70.80 | 0.050 |
| $Pd_{0.4}Ru_{0.4}O_{1.2}$/ ZSM-5 (50) | 290 | 0.09 | 68.99 | 0.062 |
| $Pd_{0.4}Ru_{0.4}O_{1.2}$/ ZSM-5 (50) | 295 | 0.10 | 68.87 | 0.069 |
| $Pd_{0.4}Ru_{0.4}O_{1.2}$/ ZSM-5 (50) | 300 | 0.14 | 62.00 | 0.087 |
| $Pd_{0.4}Ru_{0.4}O_{1.2}$/ $Al_2O_3$ | 280 | 0.05 | 56.00 | 0.028 |
| $Pd_{0.4}Ru_{0.4}O_{1.2}$/ $Al_2O_3$ | 290 | 0.07 | 56.00 | 0.039 |
| $Pd_{0.4}Ru_{0.4}O_{1.2}$/ $Al_2O_3$ | 300 | 0.10 | 56.00 | 0.056 |
| $Pd_{0.4}Ru_{0.4}O_{1.2}$/ $Al_2O_3$ | 310 | 0.15 | 55.00 | 0.083 |
| $Pd_{0.4}Ru_{0.4}O_{1.2}$/ USY (30) | 300 | 0.03 | 43.00 | 0.013 |
| $Pd_{0.4}Ru_{0.4}O_{1.2}$/ USY (30) | 310 | 0.04 | 45.62 | 0.018 |
| $Pd_{0.4}Ru_{0.4}O_{1.2}$/ USY (30) | 320 | 0.05 | 43.90 | 0.022 |
| $Pd_{0.4}Ru_{0.4}O_{1.2}$/ USY (30) | 330 | 0.08 | 41.41 | 0.033 |
| $Pd_{0.6}Ru_{0.6}O_{1.8}$/ ZSM-5 (50) | 285 | 0.05 | 66.00 | 0.033 |
| $Pd_{0.6}Ru_{0.6}O_{1.8}$/ | 290 | 0.07 | 60.80 | 0.043 |

TABLE 9-continued

| Catalyst | Reaction temperature (° C.) | Conversion ratio (%) | Selectivity (%) | Yield (%) |
|---|---|---|---|---|
| ZSM-5 (50) | | | | |
| $Pd_{0.6}Ru_{0.6}O_{1.8}$/ ZSM-5 (50) | 295 | 0.08 | 60.52 | 0.048 |
| $Pd_{0.6}Ru_{0.6}O_{1.8}$/ ZSM-5 (50) | 300 | 0.09 | 59.72 | 0.054 |

TABLE 9-continued

| Catalyst | Reaction temperature (° C.) | Conversion ratio (%) | Selectivity (%) | Yield (%) |
|---|---|---|---|---|
| $Pd_{0.4}Ru_{0.4}O_{1.2}$/ USY (30) | 300 | 0.05 | 23.00 | 0.012 |
| $Pd_{0.4}Ru_{0.4}O_{1.2}$/ USY (30) | 310 | 0.06 | 28.04 | 0.017 |
| $Pd_{0.4}Ru_{0.4}O_{1.2}$/ USY (30) | 320 | 0.07 | 29.99 | 0.021 |
| $Pd_{0.4}Ru_{0.4}O_{1.2}$/ β (38) | 280 | 0.04 | 39.00 | 0.016 |
| $Pd_{0.4}Ru_{0.4}O_{1.2}$/ β (38) | 300 | 0.09 | 41.00 | 0.037 |
| 50% $Pd_{0.2}Ru_{0.2}O_{0.6}$/ $SiO_2$ + 50% ZSM-5 (50) | 240 | 0.04 | 66.00 | 0.026 |
| 50% $Pd_{0.2}Ru_{0.2}O_{0.6}$/ $SiO_2$ + 50% ZSM-5 (50) | 250 | 0.05 | 60.00 | 0.030 |
| 50% $Pd_{0.2}Ru_{0.2}O_{0.6}$/ $SiO_2$ + 50% ZSM-5 (50) | 260 | 0.06 | 54.00 | 0.032 |

Experimental Example I

The experiment was performed in the same manner as in Experimental Example A, except that the supported catalyst was changed to a hybrid catalyst described in Table 10. Also in cases where a hybrid catalyst was used, the amount of the catalyst was 500 mg in total.

In some examples described in Table 10, not only the catalyst but also the reaction temperature were changed.

TABLE 10

| Catalyst | Reaction temperature (° C.) | Conversion ratio (%) | Selectivity (%) | Yield (%) |
|---|---|---|---|---|
| 80% $Pd_{0.4}Ru_{0.4}O_{1.2}$/ZSM-5 (50) + 20% $Al_2O_3$ | 300 | 0.12 | 64.64 | 0.078 |
| 95% $Pd_{0.4}Ru_{0.4}O_{1.2}$/$Al_2O_3$ + 5% ZSM-5 (50) | 300 | 0.11 | 55.26 | 0.061 |
| 70% $Pd_{0.4}Ru_{0.4}O_{1.2}$/$Al_2O_3$ + 30% ZSM-5 (50) | 300 | 0.12 | 55.00 | 0.066 |
| 90% $Pd_{0.3}Ru_{0.3}O_{0.9}$/$Al_2O_3$ + 10% ZSM-5 (50) | 300 | 0.09 | 60.94 | 0.055 |
| 80% $Pd_{0.3}Ru_{0.3}O_{0.9}$/$ZrO_2$ + 20% ZSM-5 (50) | 300 | 0.06 | 49.00 | 0.029 |
| 80% $Pd_{0.4}Ru_{0.4}O_{1.2}$/ZSM-5 (50) + 20% $ZrO_2$ | 300 | 0.31 | 34.06 | 0.106 |
| 60% $Pd_{0.4}Ru_{0.4}O_{1.2}$/ZSM-5 (50) + 40% $ZrO_2$ | 300 | 0.25 | 33.43 | 0.084 |
| 50% $Pd_{0.2}Ru_{0.2}O_{0.6}$/$SiO_2$ + 50% ZSM-5 (50) | 260 | 0.06 | 54.00 | 0.032 |

Experimental Example J

The experiment was performed in the same manner as in Experimental Example A, except that the supported catalyst was changed to a supported catalyst or a hybrid catalyst described in Table 11, and that the gas used in Experimental Example A (a gas containing, in helium, 13.4 vol % of methane, 1.7 vol % of nitrogen monoxide, and 0.7 vol % of oxygen) was changed to a gas containing, in helium, 13.4 vol % of methane and 0.7 vol % of oxygen.

TABLE 11

| Catalyst | Reaction temperature (° C.) | Conversion ratio (%) | Selectivity (%) | Yield (%) | Oxidizer |
|---|---|---|---|---|---|
| $Pd_{0.4}Ru_{0.2}O_{0.8}$/$Al_2O_3$ | 300 | 0.10 | 26.00 | 0.026 | $O_2$ |
| $Pd_{0.2}Ru_{0.4}O_{1.0}$/$Al_2O_3$ | 300 | 0.06 | 48.00 | 0.029 | $O_2$ |
| $Pd_{0.1}Ru_{0.3}O_{0.7}$/$Al_2O_3$ | 300 | 0.06 | 46.00 | 0.028 | $O_2$ |
| $Pd_{0.5}Ru_{0.5}O_{1.5}$/$Al_2O_3$ | 300 | 0.10 | 67.00 | 0.067 | $O_2$ |
| $Pd_{0.6}Ru_{0.6}O_{1.8}$/$Al_2O_3$ | 300 | 0.08 | 65.60 | 0.052 | $O_2$ |
| 90% $Pd_{0.6}Ru_{0.6}O_{1.8}$/$Al_2O_3$ + 10% USY (10) | 300 | 0.11 | 60.20 | 0.066 | $O_2$ |
| 50% $Pd_{0.6}Ru_{0.6}O_{1.8}$/$Al_2O_3$ + 50% $Al_2O_3$ | 300 | 0.09 | 36.60 | 0.033 | $O_2$ |

Experimental Examples K to Q 500 mg of a given supported catalyst obtained in any one of Production Examples described above was loaded on the reactor of the above-described fixed-bed flow reaction system. Pretreatment was performed by flowing a gas containing, in helium, 3.32 vol % of methane and 3.6 vol % of oxygen at 350° C. for 30 minutes, and then the gas having the same composition was flowed into the fixed-bed flow reaction system at a temperature shown in Table to cause a reaction. The flow rate of the gas was 100 ml/min. The composition of the gas produced one hour after the start of the flowing was examined, and the selectivity (%), the conversion ratio (%), and the yield (%) were determined. The results are shown in Table 12 to 16. wt % means the ratio of the solid acid (D) to the total 100 wt % of the supported catalyst (C) and the solid acid (D).

TABLE 12

| | Reaction temperature ° C. | HCHO Selectivity % | $CH_4$ Conversion ratio % | HCHO Yield % |
|---|---|---|---|---|
| $Pd_{0.4}Ru_{0.4}O_{1.2}$/γ-$Al_2O_3$ | 300 | 40 | 0.28 | 0.11 |
| $Pd_{0.4}Ru_{0.4}O_{1.2}$/γ-$Al_2O_3$ | 310 | 42 | 0.35 | 0.15 |
| $Pd_{0.4}Ru_{0.4}O_{1.2}$/γ-$Al_2O_3$ | 320 | 40 | 0.49 | 0.19 |
| $Pd_{0.5}Ru_{0.5}O_{1.5}$/γ$Al_2O_3$ | 300 | 49 | 0.19 | 0.09 |

TABLE 12-continued

| | Reaction temperature ° C. | HCHO Selectivity % | $CH_4$ Conversion ratio % | HCHO Yield % |
|---|---|---|---|---|
| $Pd_{0.5}Ru_{0.5}O_{1.5}$/γ$Al_2O_3$ | 310 | 46 | 0.29 | 0.13 |
| $Pd_{0.5}Ru_{0.5}O_{1.5}$/γ$Al_2O_3$ | 320 | 44 | 0.41 | 0.18 |
| $Pd_{0.6}Ru_{0.6}O_{1.8}$/γ-$Al_2O_3$ | 300 | 52 | 0.19 | 0.10 |
| $Pd_{0.6}Ru_{0.6}O_{1.8}$/γ-$Al_2O_3$ | 310 | 49 | 0.29 | 0.14 |
| $Pd_{0.6}Ru_{0.6}O_{1.8}$/γ-$Al_2O_3$ | 320 | 44 | 0.43 | 0.19 |
| $Pd_{0.7}Ru_{0.7}O_{2.1}$/γ-$Al_2O_3$ | 300 | 47 | 0.21 | 0.10 |
| $Pd_{0.7}Ru_{0.7}O_{2.1}$/γ-$Al_2O_3$ | 310 | 44 | 0.29 | 0.13 |
| $Pd_{0.7}Ru_{0.7}O_{2.1}$/γ-$Al_2O_3$ | 320 | 41 | 0.41 | 0.17 |
| $Pd_{0.8}Ru_{0.8}O_{2.4}$/γ-$Al_2O_3$ | 300 | 35 | 0.29 | 0.10 |
| $Pd_{0.8}Ru_{0.8}O_{2.4}$/γ-$Al_2O_3$ | 310 | 28 | 0.46 | 0.13 |
| $Pd_{0.8}Ru_{0.8}O_{2.4}$/γ-$Al_2O_3$ | 320 | 24 | 0.66 | 0.16 |

TABLE 13

| | Reaction temperature ° C. | HCHO Selectivity % | $CH_4$ Conversion ratio % | HCHO Yield % |
|---|---|---|---|---|
| $Pd_{0.7}Ru_{0.7}O_{2.1}/\gamma\text{-}Al_2O_3$ | 300 | 47 | 0.21 | 0.10 |
| $Pd_{0.7}Ru_{0.7}O_{2.1}/\gamma\text{-}Al_2O_3$ | 310 | 44 | 0.29 | 0.13 |
| $Pd_{0.7}Ru_{0.7}O_{2.1}/\gamma\text{-}Al_2O_3$ | 320 | 41 | 0.41 | 0.17 |
| $Pd_{0.7}Ru_{0.7}O_{2.1}/\gamma\text{-}Al_2O_3$ + 10 wt % USY (10) | 300 | 47 | 0.27 | 0.13 |
| $Pd_{0.7}Ru_{0.7}O_{2.1}/\gamma\text{-}Al_2O_3$ + 10 wt % USY (10) | 310 | 42 | 0.42 | 0.18 |
| $Pd_{0.7}Ru_{0.7}O_{2.1}/\gamma\text{-}Al_2O_3$ + 10 wt % USY (10) | 320 | 38 | 0.58 | 0.22 |
| $Pd_{0.7}Ru_{0.7}O_{2.1}/\gamma\text{-}Al_2O_3$ + 10 wt % USY (20) | 300 | 45 | 0.29 | 0.13 |
| $Pd_{0.7}Ru_{0.7}O_{2.1}/\gamma\text{-}Al_2O_3$ + 10 wt % USY (20) | 310 | 42 | 0.38 | 0.16 |
| $Pd_{0.7}Ru_{0.7}O_{2.1}/\gamma\text{-}Al_2O_3$ + 10 wt % USY (20) | 320 | 39 | 0.53 | 0.21 |
| $Pd_{0.7}Ru_{0.7}O_{2.1}/\gamma\text{-}Al_2O_3$ + 10 wt % USY (30) | 300 | 52 | 0.24 | 0.12 |
| $Pd_{0.7}Ru_{0.7}O_{2.1}/\gamma\text{-}Al_2O_3$ + 10 wt % USY (30) | 310 | 51 | 0.33 | 0.17 |
| $Pd_{0.7}Ru_{0.7}O_{2.1}/\gamma\text{-}Al_2O_3$ + 10 wt % USY (30) | 320 | 48 | 0.48 | 0.23 |
| $Pd_{0.7}Ru_{0.7}O_{2.1}/\gamma\text{-}Al_2O_3$ + 10 wt % USY (70) | 300 | 49 | 0.24 | 0.12 |
| $Pd_{0.7}Ru_{0.7}O_{2.1}/\gamma\text{-}Al_2O_3$ + 10 wt % USY (70) | 310 | 45 | 0.35 | 0.16 |
| $Pd_{0.7}Ru_{0.7}O_{2.1}/\gamma\text{-}Al_2O_3$ + 10 wt % USY (70) | 320 | 41 | 0.51 | 0.21 |

TABLE 14

| | Reaction temperature ° C. | HCHO Selectivity % | $CH_4$ Conversion ratio % | HCHO Yield % |
|---|---|---|---|---|
| $Pd_{0.7}Ru_{0.7}O_{2.1}/\gamma\text{-}Al_2O_3$ | 300 | 47 | 0.21 | 0.10 |
| $Pd_{0.7}Ru_{0.7}O_{2.1}/\gamma\text{-}Al_2O_3$ | 310 | 44 | 0.29 | 0.13 |
| $Pd_{0.7}Ru_{0.7}O_{2.1}/\gamma\text{-}Al_2O_3$ | 320 | 41 | 0.41 | 0.17 |
| $Pd_{0.7}Ru_{0.7}O_{2.1}/\gamma\text{-}Al_2O_3$ + 5 wt % USY (30) | 300 | 51 | 0.24 | 0.12 |
| $Pd_{0.7}Ru_{0.7}O_{2.1}/\gamma\text{-}Al_2O_3$ + 5 wt % USY (30) | 310 | 47 | 0.36 | 0.17 |
| $Pd_{0.7}Ru_{0.7}O_{2.1}/\gamma\text{-}Al_2O_3$ + 5 wt % USY (30) | 320 | 45 | 0.51 | 0.23 |
| $Pd_{0.7}Ru_{0.7}O_{2.1}/\gamma\text{-}Al_2O_3$ + 10 wt % USY (30) | 300 | 52 | 0.24 | 0.12 |
| $Pd_{0.7}Ru_{0.7}O_{2.1}/\gamma\text{-}Al_2O_3$ + 10 wt % USY (30) | 310 | 51 | 0.33 | 0.17 |
| $Pd_{0.7}Ru_{0.7}O_{2.1}/\gamma\text{-}Al_2O_3$ + 10 wt % USY (30) | 320 | 48 | 0.48 | 0.23 |
| $Pd_{0.7}Ru_{0.7}O_{2.1}/\gamma\text{-}Al_2O_3$ + 15 wt % USY (30) | 300 | 50 | 0.22 | 0.11 |
| $Pd_{0.7}Ru_{0.7}O_{2.1}/\gamma\text{-}Al_2O_3$ + 15 wt % USY (30) | 310 | 48 | 0.32 | 0.15 |
| $Pd_{0.7}Ru_{0.7}O_{2.1}/\gamma\text{-}Al_2O_3$ + 15 wt % USY (30) | 320 | 44 | 0.47 | 0.21 |
| $Pd_{0.7}Ru_{0.7}O_{2.1}/\gamma\text{-}Al_2O_3$ + 20 wt % USY (30) | 300 | 49 | 0.26 | 0.13 |
| $Pd_{0.7}Ru_{0.7}O_{2.1}/\gamma\text{-}Al_2O_3$ + 20 wt % USY (30) | 310 | 45 | 0.39 | 0.18 |
| $Pd_{0.7}Ru_{0.7}O_{2.1}/\gamma\text{-}Al_2O_3$ + 20 wt % USY (30) | 320 | 42 | 0.56 | 0.23 |

TABLE 15

| | Reaction temperature ° C. | HCHO Selectivity % | CH$_4$ Conversion ratio % | HCHO Yield % |
|---|---|---|---|---|
| Pd$_{0.6}$Ru$_{0.6}$O$_{1.8}$/γ-Al$_2$O$_3$ | 300 | 52 | 0.19 | 0.10 |
| Pd$_{0.6}$Ru$_{0.6}$O$_{1.8}$/γ-Al$_2$O$_3$ | 310 | 49 | 0.29 | 0.14 |
| Pd$_{0.6}$Ru$_{0.6}$O$_{1.8}$/γ-Al$_2$O$_3$ | 320 | 44 | 0.43 | 0.19 |
| Pd$_{0.6}$Ru$_{0.6}$O$_{1.8}$/γ-Al$_2$O$_3$ + 10 wt % USY (30) | 300 | 52 | 0.21 | 0.11 |
| Pd$_{0.6}$Ru$_{0.6}$O$_{1.8}$/γ-Al$_2$O$_3$ + 10 wt % USY (30) | 310 | 52 | 0.30 | 0.16 |
| Pd$_{0.6}$Ru$_{0.6}$O$_{1.8}$/γ-Al$_2$O$_3$ + 10 wt % USY (30) | 320 | 49 | 0.44 | 0.22 |
| Pd$_{0.6}$Ru$_{0.6}$O$_{1.8}$/γ-Al$_2$O$_3$ + 20 wt % USY (30) | 300 | 59 | 0.17 | 0.10 |
| Pd$_{0.6}$Ru$_{0.6}$O$_{1.8}$/γ-Al$_2$O$_3$ + 20 wt % USY (30) | 310 | 57 | 0.26 | 0.15 |
| Pd$_{0.6}$Ru$_{0.6}$O$_{1.8}$/γ-Al$_2$O$_3$ + 20 wt % USY (30) | 320 | 54 | 0.38 | 0.21 |
| Pd$_{0.6}$Ru$_{0.6}$O$_{1.8}$/γ-Al$_2$O$_3$ + 20 wt % USY (30) | 330 | 49 | 0.55 | 0.27 |
| Pd$_{0.6}$Ru$_{0.6}$O$_{1.8}$/γ-Al$_2$O$_3$ + 20 wt % USY (10) | 300 | 55 | 0.16 | 0.09 |
| Pd$_{0.6}$Ru$_{0.6}$O$_{1.8}$/γ-Al$_2$O$_3$ + 20 wt % USY (10) | 310 | 52 | 0.25 | 0.13 |
| Pd$_{0.6}$Ru$_{0.6}$O$_{1.8}$/γ-Al$_2$O$_3$ + 20 wt % USY (10) | 320 | 49 | 0.36 | 0.18 |
| Pd$_{0.6}$Ru$_{0.6}$O$_{1.8}$/γ-Al$_2$O$_3$ + 30 wt % USY (30) | 300 | 46 | 0.19 | 0.09 |
| Pd$_{0.6}$Ru$_{0.6}$O$_{1.8}$/γ-Al$_2$O$_3$ + 30 wt % USY (30) | 310 | 47 | 0.26 | 0.12 |
| Pd$_{0.6}$Ru$_{0.6}$O$_{1.8}$/γ-Al$_2$O$_3$ + 30 wt % USY (30) | 320 | 46 | 0.38 | 0.17 |

TABLE 16

| | Reaction temperature ° C. | HCHO Selectivity % | CH$_4$ Conversion ratio % | HCHO Yield % |
|---|---|---|---|---|
| Pd$_{0.6}$Ru$_{0.6}$O$_{1.8}$/γ-Al$_2$O$_3$ | 300 | 52 | 0.19 | 0.10 |
| Pd$_{0.6}$Ru$_{0.6}$O$_{1.8}$/γ-Al$_2$O$_3$ | 310 | 49 | 0.29 | 0.14 |
| Pd$_{0.6}$Ru$_{0.6}$O$_{1.8}$/γ-Al$_2$O$_3$ | 320 | 44 | 0.43 | 0.19 |
| Pd$_{0.6}$Ru$_{0.6}$O$_{1.8}$/γ-Al$_2$O$_3$ + 20 wt % ZMS-5 (50) | 300 | 57 | 0.20 | 0.11 |
| Pd$_{0.6}$Ru$_{0.6}$O$_{1.8}$/γ-Al$_2$O$_3$ + 20 wt % ZMS-5 (50) | 310 | 53 | 0.30 | 0.16 |
| Pd$_{0.6}$Ru$_{0.6}$O$_{1.8}$/γ-Al$_2$O$_3$ + 20 wt % ZMS-5 (50) | 320 | 48 | 0.44 | 0.21 |
| Pd$_{0.6}$Ru$_{0.6}$O$_{1.8}$/γ-Al$_2$O$_3$ + 20 wt % ZMS-5 (80) | 300 | 55 | 0.24 | 0.13 |
| Pd$_{0.6}$Ru$_{0.6}$O$_{1.8}$/γ-Al$_2$O$_3$ + 20 wt % ZMS-5 (80) | 310 | 53 | 0.35 | 0.19 |
| Pd$_{0.6}$Ru$_{0.6}$O$_{1.8}$/γ-Al$_2$O$_3$ + 20 wt % ZMS-5 (80) | 320 | 48 | 0.52 | 0.25 |
| Pd$_{0.6}$Ru$_{0.6}$O$_{1.8}$/γ-Al$_2$O$_3$ + 20 wt % ZMS-5 (280) | 300 | 55 | 0.20 | 0.11 |
| Pd$_{0.6}$Ru$_{0.6}$O$_{1.8}$/γ-Al$_2$O$_3$ + 20 wt % ZMS-5 (280) | 310 | 54 | 0.30 | 0.16 |
| Pd$_{0.6}$Ru$_{0.6}$O$_{1.8}$/γ-Al$_2$O$_3$ + 20 wt % ZMS-5 (280) | 320 | 50 | 0.43 | 0.22 |
| Pd$_{0.6}$Ru$_{0.6}$O$_{1.8}$/γ-Al$_2$O$_3$ + 20 wt % ZMS-5 (280) | 330 | 46 | 0.63 | 0.29 |

Experimental Example R

A given supported catalyst obtained in any one of Production Examples described above was loaded in an amount used as described in Table 17 on the reactor of the above-described fixed-bed flow reaction system. Pretreatment was performed by flowing a gas containing, in helium, 1.6 vol % of methane and 1.6 vol % of oxygen at 350° C. for 30 minutes, and then the gas having the same composition was flowed into the fixed-bed flow reaction system at a temperature shown in Table to cause a reaction. The flow rate of the gas was 100 ml/min. The composition of the gas produced one hour after the start of the flowing was examined, and the selectivity (%), the conversion ratio (%), and the yield (%) were determined. The results are shown in Table 17.

TABLE 17

|  | Amount of catalyst used g | Reaction temperature ° C. | HCHO Selectivity % | $CH_4$ Conversion ratio % | HCHO Yield % |
|---|---|---|---|---|---|
| $Pd_{0.6}Ru_{0.6}O_{1.8}/\gamma\text{-}Al_2O_3$ | 0.25 | 300 | 44 | 0.13 | 0.06 |
| $Pd_{0.6}Ru_{0.6}O_{1.8}/\gamma\text{-}Al_2O_3$ | 0.25 | 310 | 42 | 0.21 | 0.09 |
| $Pd_{0.6}Ru_{0.6}O_{1.8}/\gamma\text{-}Al_2O_3$ | 0.25 | 320 | 39 | 0.32 | 0.13 |
| $Pd_{0.6}Ru_{0.6}O_{1.8}/\gamma\text{-}Al_2O_3$ | 0.5 | 300 | 48 | 0.25 | 0.12 |
| $Pd_{0.6}Ru_{0.6}O_{1.8}/\gamma\text{-}Al_2O_3$ | 0.5 | 310 | 46 | 0.37 | 0.17 |
| $Pd_{0.6}Ru_{0.6}O_{1.8}/\gamma\text{-}Al_2O_3$ | 0.5 | 320 | 42 | 0.54 | 0.23 |
| $Pd_{0.6}Ru_{0.6}O_{1.8}/\gamma\text{-}Al_2O_3$ | 0.75 | 300 | 48 | 0.31 | 0.15 |
| $Pd_{0.6}Ru_{0.6}O_{1.8}/\gamma\text{-}Al_2O_3$ | 0.75 | 310 | 44 | 0.47 | 0.21 |
| $Pd_{0.6}Ru_{0.6}O_{1.8}/\gamma\text{-}Al_2O_3$ | 0.75 | 320 | 40 | 0.68 | 0.27 |

Experimental Example 5

500 mg of a given supported catalyst obtained in any one of Production Examples described above was loaded on the reactor of the above-described fixed-bed flow reaction system. Pretreatment was performed by flowing a gas containing, in helium, 3.32 vol % of methane and 3.6 vol % of oxygen at 350° C. for 30 minutes, and then the gas having the same composition was flowed into the fixed-bed flow reaction system at a temperature and a pressure shown in Table 18 to cause a reaction. The flow rate of the gas was 100 ml/min. The composition of the gas produced one hour after the start of the flowing was examined, and the selectivity (%), the conversion ratio (%), and the yield (%) were determined. The results are shown in Table 18.

TABLE 18

|  | Reaction temperature ° C. | Reaction pressure MPa | HCHO Selectivity % | $CH_4$ Conversion ratio % | HCHO Yield % |
|---|---|---|---|---|---|
| $Pd_{0.6}Ru_{0.6}O_{1.8}/\gamma\text{-}Al_2O_3$ | 240 | 0.4 | 46.8 | 0.09 | 0.04 |
| $Pd_{0.6}Ru_{0.6}O_{1.8}/\gamma\text{-}Al_2O_3$ | 260 | 0.1 | 45.0 | 0.08 | 0.03 |
| $Pd_{0.6}Ru_{0.6}O_{1.8}/\gamma\text{-}Al_2O_3$ | 260 | 0.2 | 48.0 | 0.09 | 0.04 |
| $Pd_{0.6}Ru_{0.6}O_{1.8}/\gamma\text{-}Al_2O_3$ | 260 | 0.3 | 49.0 | 0.15 | 0.07 |
| $Pd_{0.6}Ru_{0.6}O_{1.8}/\gamma\text{-}Al_2O_3$ | 260 | 0.4 | 44.0 | 0.21 | 0.09 |
| $Pd_{0.6}Ru_{0.6}O_{1.8}/\gamma\text{-}Al_2O_3$ | 280 | 0.1 | 50.2 | 0.14 | 0.07 |
| $Pd_{0.6}Ru_{0.6}O_{1.8}/\gamma\text{-}Al_2O_3$ | 280 | 0.2 | 51.6 | 0.22 | 0.11 |

Example

A supported catalyst shown below was prepared in the same manner as in Production Examples described above, and loaded on the reactor of the above-described fixed-bed flow reaction system. The supported catalyst was pretreated with helium gas at 350° C. in the conditions shown below, and then the gas having the same composition was flowed into the fixed-bed flow reaction system at a temperature shown in Table to cause a reaction. The flow rate of the gas was 100 ml/min. The composition of the gas produced one hour after the start of the flowing was examined, and the selectivity (%), the conversion ratio (%), and the yield (%) were determined. The results are shown in Table below. The data of some of Examples are repeated.

TABLE 19

| | Composition of components of bimetallic oxide (A): $A_mB_nO_x$ Lower row: ratio between $m$, $n$, and $x$ | | | Support | Solid acid | Composition of oxidizing gas (vol %) | | | Reaction temperature | $CH_4$ Conversion ratio | HCHO Selectivity | HCHO Yield |
|---|---|---|---|---|---|---|---|---|---|---|---|---|
| Example | A | B | O | (B) | (D) | $CH_4$ | NO | $O_2$ | (° C.) | (%) | (%) | (%) |
| 51 | Ir | Ru | O | $\eta\text{-}Al_2O_3$ | | 13.4 | | 0.7 | 300 | 0.22 | 14.00 | 0.031 |
| | 0.4 | 0.4 | 1.6 | | | | | | | | | |
| 52 | Pd | Ir | O | $\eta\text{-}Al_2O_3$ | | 13.4 | | 0.7 | 300 | 0.06 | 12.78 | 0.008 |
| | 0.4 | 0.4 | 1.2 | | | | | | | | | |

TABLE 19-continued

| Example | Composition of components of bimetallic oxide (A): $A_mB_nO_x$ Lower row: ratio between $m$, $n$, and $x$ | | | Support (B) | Solid acid (D) | Composition of oxidizing gas (vol %) | | | Reaction temperature (° C.) | $CH_4$ Conversion ratio (%) | HCHO Selectivity (%) | HCHO Yield (%) |
|---|---|---|---|---|---|---|---|---|---|---|---|---|
| | A | B | O | | | $CH_4$ | NO | $O_2$ | | | | |
| 53 | Pt 0.1 | Ru 0.1 | O 0.3 | η-Al$_2$O$_3$ | | 13.4 | | 0.7 | 300 | 0.3 | 20.51 | 0.062 |
| 54 | Pt 0.2 | Ir 0.2 | O 0.6 | η-Al$_2$O$_3$ | | 13.4 | | 0.7 | 300 | 0.31 | 10.97 | 0.034 |
| 55 | Pd 0.4 | Ru 0.4 | O 1.2 | η-Al$_2$O$_3$ | | 13.4 | | 0.7 | 300 | 0.14 | 40 | 0.056 |
| 56 | Pd 0.1 | Ru 0.3 | O 0.7 | η-Al$_2$O$_3$ | | 13.4 | | 0.7 | 300 | 0.06 | 46 | 0.028 |

Supported catalyst 0.5 g,
Reaction pressure 0.1 MPa

TABLE 20

| Example | Composition of components of bimetallic oxide (A): AmBnOx Ratio between $m$, $n$, and $x$ | | | Support (B) | Solid acid (D) | Composition of oxidizing gas (vol %) | | | Reaction temperature (° C.) | $CH_4$ Conversion ratio (%) | HCHO Selectivity (%) | HCHO Yield (%) |
|---|---|---|---|---|---|---|---|---|---|---|---|---|
| | Pd | Ru | O | | | $CH_4$ | NO | $O_2$ | | | | |
| 61 | 0.4 | 0.4 | 1.2 | ZSM-5 (50) | | 13.4 | 1.7 | 0.7 | 300 | 0.14 | 62.00 | 0.087 |
| Comparative example 1 | | 0.4 | 0.6 | ZSM-5 (50) | | 13.4 | 1.7 | 0.7 | 300 | 0.06 | 15.78 | 0.009 |
| Comparative example 2 | 0.4 | | 0.6 | ZSM-5 (50) | | 13.4 | 1.7 | 0.7 | 300 | 0.43 | 0.48 | 0.002 |
| Comparative example 3 | | | | ZSM-5 (50) | | 13.4 | 1.7 | 0.7 | 300 | 0.10 | 0.00 | 0.000 |
| 65 | 0.3 | 0.3 | 0.9 | η-Al$_2$O$_3$ | | 13.4 | 1.7 | 0.7 | 300 | 0.08 | 60 | 0.048 |
| Comparative example 4 | 0.3 | | 0.45 | η-Al$_2$O$_3$ | | 13.4 | 1.7 | 0.7 | 300 | 0.28 | 1 | 0.003 |
| Comparative example 5 | | 0.3 | 0.45 | η-Al$_2$O$_3$ | | 13.4 | 1.7 | 0.7 | 300 | 0.04 | 9 | 0.004 |

Supported catalyst 0.5 g,
Reaction pressure 0.1 MPa

TABLE 21

| Example | Composition of components of bimetallic oxide (A): AmBnOx Ratio between $m$, $n$, and $x$ | | | Support (B) | Solid acid (D) | Composition of oxidizing gas (vol %) | | | Reaction temperature (° C.) | $CH_4$ Conversion ratio (%) | HCHO Selectivity (%) | HCHO Yield (%) |
|---|---|---|---|---|---|---|---|---|---|---|---|---|
| | Pd | Ru | O | | | $CH_4$ | NO | $O_2$ | | | | |
| 71 | 0.4 | 0.4 | 1.2 | ZSM-5 (50) | | 13.4 | 1.7 | 0.7 | 300 | 0.14 | 62.00 | 0.087 |
| 72 | 0.4 | 0.4 | 1.2 | η-Al$_2$O$_3$ | | 13.4 | 1.7 | 0.7 | 300 | 0.10 | 56.24 | 0.056 |
| 73 | 0.4 | 0.4 | 1.2 | USY (30) | | 13.4 | 1.7 | 0.7 | 300 | 0.03 | 43.00 | 0.013 |
| 74 | 0.4 | 0.4 | 1.2 | USY (30) | | 13.4 | 1.7 | 0.7 | 300 | 0.05 | 23.00 | 0.012 |
| 75 | 0.4 | 0.4 | 1.2 | β (38) | | 13.4 | 1.7 | 0.7 | 300 | 0.09 | 41.00 | 0.037 |
| 76 | 0.3 | 0.3 | 0.9 | η-Al$_2$O$_3$ | | 13.4 | 1.7 | 0.7 | 300 | 0.08 | 60.00 | 0.048 |
| 77 | 0.3 | 0.3 | 0.9 | TiO$_2$ | | 13.4 | 1.7 | 0.7 | 300 | 0.05 | 42.00 | 0.021 |
| 78 | 0.3 | 0.3 | 0.9 | SiO$_2$—Al$_2$O$_3$ | | 13.4 | 1.7 | 0.7 | 300 | 0.06 | 51.00 | 0.031 |
| 79 | 0.3 | 0.3 | 0.9 | ZrO$_2$ | | 13.4 | 1.7 | 0.7 | 300 | 0.03 | 45.00 | 0.014 |
| 80 | 0.3 | 0.3 | 0.9 | CeO$_2$ | | 13.4 | 1.7 | 0.7 | 300 | 0.01 | 40.00 | 0.004 |

TABLE 21-continued

| Example | Composition of components of bimetallic oxide (A): AmBnOx Ratio between m, n, and x | | | Support (B) | Solid acid (D) | Composition of oxidizing gas (vol %) | | | Reaction temperature (° C.) | CH₄ Conversion ratio (%) | HCHO Selectivity (%) | HCHO Yield (%) |
|---|---|---|---|---|---|---|---|---|---|---|---|---|
| | Pd | Ru | O | | | CH₄ | NO | O₂ | | | | |
| 81 | 0.2 | 0.2 | 0.6 | SiO₂ | | 13.4 | 1.7 | 0.7 | 250 | 0.01 | 16.00 | 0.002 |
| 82 | 0.4 | 0.4 | 1.2 | ZSM-5 (50) | | 13.4 | 1.7 | 0.7 | 300 | 0.14 | 62.00 | 0.087 |
| 83 | 0.6 | 0.6 | 1.8 | ZSM-5 (50) | | 13.4 | 1.7 | 0.7 | 300 | 0.09 | 59.72 | 0.054 |

Supported catalyst 0.5 g,
Reaction pressure 0.1 MPa

TABLE 22

| Example | Composition of components of bimetallic oxide (A): AmBnOx Ratio between m, n, and x | | | Support (B) | Solid acid (D) | Composition of oxidizing gas (vol %) | | | Reaction temperature (° C.) | CH₄ Conversion ratio (%) | HCHO Selectivity (%) | HCHO Yield (%) |
|---|---|---|---|---|---|---|---|---|---|---|---|---|
| | Pd | Ru | O | | | CH₄ | NO | O₂ | | | | |
| 91 | 0.4 | 0.4 | 1.2 | ZSM-5 (50) | | 13.4 | 1.7 | 0.7 | 300 | 0.14 | 62.00 | 0.087 |
| 92 | 0.4 | 0.4 | 1.2 | ZSM-5 (50) | 20% η-Al₂O₃ | 13.4 | 1.7 | 0.7 | 300 | 0.12 | 64.64 | 0.078 |
| 93 | 0.4 | 0.4 | 1.2 | ZSM-5 (50) | | 13.4 | 1.7 | 0.7 | 300 | 0.14 | 52.00 | 0.073 |
| 94 | 0.4 | 0.4 | 1.2 | ZSM-5 (50) | 20% ZrO₂ | 13.4 | 1.7 | 0.7 | 300 | 0.31 | 34.06 | 0.106 |
| 95 | 0.4 | 0.4 | 1.2 | ZSM-5 (50) | 40% ZrO₂ | 13.4 | 1.7 | 0.7 | 300 | 0.25 | 33.43 | 0.084 |
| 96 | 0.4 | 0.4 | 1.2 | Al₂O₃ | | 13.4 | 1.7 | 0.7 | 300 | 0.10 | 56.24 | 0.056 |
| 97 | 0.4 | 0.4 | 1.2 | Al₂O₃ | 5% ZSM-5 (50) | 13.4 | 1.7 | 0.7 | 300 | 0.11 | 55.26 | 0.061 |
| 98 | 0.4 | 0.4 | 1.2 | Al₂O₃ | 30% ZSM-5 (50) | 13.4 | 1.7 | 0.7 | 300 | 0.12 | 55.00 | 0.066 |
| 99 | 0.3 | 0.3 | 0.9 | Al₂O₃ | | 13.4 | 1.7 | 0.7 | 300 | 0.08 | 60.00 | 0.048 |
| 100 | 0.3 | 0.3 | 0.9 | Al₂O₃ | 10% ZSM-5 (50) | 13.4 | 1.7 | 0.7 | 300 | 0.09 | 60.94 | 0.055 |
| 101 | 0.3 | 0.3 | 0.9 | TiO₂ | | 13.4 | 1.7 | 0.7 | 300 | 0.05 | 42.00 | 0.021 |
| 102 | 0.3 | 0.3 | 0.9 | TiO₂ | 5% ZSM-5 (50) | 13.4 | 1.7 | 0.7 | 300 | 0.06 | 43.00 | 0.026 |
| 103 | 0.3 | 0.3 | 0.9 | TiO₂ | 10% ZSM-5 (50) | 13.4 | 1.7 | 0.7 | 300 | 0.09 | 43.00 | 0.039 |
| 104 | 0.3 | 0.3 | 0.9 | SiO₂—Al₂O₃ | | 13.4 | 1.7 | 0.7 | 300 | 0.06 | 51.00 | 0.031 |
| 105 | 0.3 | 0.3 | 0.9 | SiO₂—Al₂O₃ | 10% ZSM-5 (50) | 13.4 | 1.7 | 0.7 | 300 | 0.06 | 52.00 | 0.031 |
| 106 | 0.3 | 0.3 | 0.9 | SiO₂—Al₂O₃ | 20% ZSM-5 (50) | 13.4 | 1.7 | 0.7 | 300 | 0.07 | 54.00 | 0.038 |
| 107 | 0.3 | 0.3 | 0.9 | CeO₂ | | 13.4 | 1.7 | 0.7 | 300 | 0.01 | 40.00 | 0.004 |
| 108 | 0.3 | 0.3 | 0.9 | CeO₂ | 10% ZSM-5 (50) | 13.4 | 1.7 | 0.7 | 300 | 0.03 | 46.00 | 0.014 |
| 109 | 0.3 | 0.3 | 0.9 | CeO₂ | 20% ZSM-5 (50) | 13.4 | 1.7 | 0.7 | 300 | 0.04 | 51.55 | 0.021 |
| 110 | 0.3 | 0.3 | 0.9 | CeO₂ | 30% ZSM-5 (50) | 13.4 | 1.7 | 0.7 | 300 | 0.04 | 54.05 | 0.022 |
| 111 | 0.3 | 0.3 | 0.9 | ZrO₂ | | 13.4 | 1.7 | 0.7 | 300 | 0.03 | 45.00 | 0.014 |
| 112 | 0.3 | 0.3 | 0.9 | ZrO₂ | 10% ZSM-5 (50) | 13.4 | 1.7 | 0.7 | 300 | 0.05 | 45.00 | 0.023 |
| 113 | 0.3 | 0.3 | 0.9 | ZrO₂ | 20% ZSM-5 (50) | 13.4 | 1.7 | 0.7 | 300 | 0.06 | 49.00 | 0.029 |
| 114 | 0.2 | 0.2 | 0.6 | SiO₂ | | 13.4 | 1.7 | 0.7 | 250 | 0.01 | 16.00 | 0.002 |
| 115 | 0.2 | 0.2 | 0.6 | SiO₂ | 50% ZSM-5 (50) | 13.4 | 1.7 | 0.7 | 240 | 0.04 | 66.00 | 0.026 |
| 116 | 0.2 | 0.2 | 0.6 | SiO₂ | 50% ZSM-5 (50) | 13.4 | 1.7 | 0.7 | 250 | 0.05 | 60.00 | 0.030 |
| 117 | 0.2 | 0.2 | 0.6 | SiO₂ | 50% ZSM-5 (50) | 13.4 | 1.7 | 0.7 | 260 | 0.06 | 54.00 | 0.032 |

Supported catalyst 0.5 g,
Reaction pressure 0.1 MPa

TABLE 23

| | Composition of components of bimetallic oxide (A): A$m$B$n$O$x$ Ratio between $m$, $n$, and $x$ | | | Support | Solid acid | Composition of oxidizing gas (vol %) | | | Reaction temperature | CH$_4$ Conversion ratio | HCHO Selectivity | HCHO Yield |
|---|---|---|---|---|---|---|---|---|---|---|---|---|
| Example | Pd | Ru | O | (B) | (D) | CH$_4$ | NO | O$_2$ | (° C.) | (%) | (%) | (%) |
| 121 | 0.4 | 0.4 | 1.2 | ZSM-5 (50) | | 13.4 | 1.7 | 0.7 | 300 | 0.14 | 62.00 | 0.087 |
| 122 | 0.4 | 0.4 | 1.2 | ZSM-5 (50) | | 13.4 | 1.7 | 0.7 | 300 | 0.08 | 32.00 | 0.026 |
| 123 | 0.4 | 0.4 | 1.2 | USY (30) | | 13.4 | 1.7 | 0.7 | 300 | 0.03 | 43.00 | 0.013 |
| 124 | 0.4 | 0.4 | 1.2 | USY (30) | | 13.4 | 1.7 | 0.7 | 300 | 0.05 | 22.71 | 0.011 |

Supported catalyst 0.5 g,
Reaction pressure 0.1 MPa

TABLE 24

| | Composition of components of bimetallic oxide (A): A$m$B$n$O$x$ Ratio between $m$, $n$, and $x$ | | | Support | Solid acid | Composition of oxidizing gas (vol %) | | | Reaction temperature | CH$_4$ Conversion ratio | HCHO Selectivity | HCHO Yield |
|---|---|---|---|---|---|---|---|---|---|---|---|---|
| Example | Pd | Ru | O | (B) | (D) | CH$_4$ | NO | O$_2$ | (° C.) | (%) | (%) | (%) |
| 131 | 0.3 | 0.3 | 0.9 | η-Al$_2$O$_3$ | | 13.4 | 1.7 | 0.7 | 300 | 0.08 | 60.00 | 0.048 |
| 132 | 0.3 | 0.3 | 0.9 | η-Al$_2$O$_3$ | | 13.4 | | 0.7 | 300 | 0.08 | 55.00 | 0.044 |
| 133 | 0.3 | 0.3 | 0.9 | η-Al$_2$O$_3$ | | 13.4 | 1.7 | 0.7 | 300 | 0.08 | 60 | 0.048 |
| 134 | 0.3 | 0.3 | 0.9 | η-Al$_2$O$_3$ | | 13.4 | | 0.7 | 300 | 0.08 | 55 | 0.044 |
| 135 | 0.3 | 0.3 | 0.9 | η-Al$_2$O$_3$ | | 13.4 | 1.7 | | 300 | 0.05 | 65 | 0.033 |
| 136 | 0.6 | 0.6 | 1.8 | η-Al$_2$O$_3$ | | 13.4 | 1.7 | 0.7 | 300 | 0.1 | 56 | 0.056 |
| 137 | 0.6 | 0.6 | 1.8 | η-Al$_2$O$_3$ | | 13.4 | | 0.7 | 300 | 0.08 | 66 | 0.053 |
| 138 | 0.6 | 0.6 | 1.8 | η-Al$_2$O$_3$ | | 13.4 | 1.7 | | 300 | 0.05 | 66 | 0.033 |
| 139 | 0.3 | 0.3 | 0.9 | ZrO$_2$ | | 13.4 | 1.7 | 0.7 | 300 | 0.03 | 45.00 | 0.014 |
| 140 | 0.3 | 0.3 | 0.9 | ZrO$_2$ | | 13.4 | | 0.7 | 300 | 0.04 | 39.00 | 0.016 |
| 141 | 0.3 | 0.3 | 0.9 | TiO$_2$ | | 13.4 | 1.7 | 0.7 | 300 | 0.05 | 42.00 | 0.021 |
| 142 | 0.3 | 0.3 | 0.9 | ZrO$_2$ | | 13.4 | | 0.7 | 300 | 0.07 | 25.51 | 0.018 |
| 143 | 0.3 | 0.3 | 0.9 | η-Al$_2$O$_3$ | | 13.4 | | 0.7 | 300 | 0.08 | 55 | 0.044 |
| 144 | 0.5 | 0.5 | 1.5 | η-Al$_2$O$_3$ | | 13.4 | | 0.7 | 300 | 0.12 | 54 | 0.065 |
| 145 | 0.6 | 0.6 | 1.8 | η-Al$_2$O$_3$ | | 13.4 | | 0.7 | 300 | 0.08 | 66 | 0.053 |
| 146 | 0.4 | 0.4 | 1.2 | γ-Al$_2$O$_3$ | | 3.32 | | 3.6 | 300 | 0.28 | 40 | 0.112 |
| 147 | 0.4 | 0.4 | 1.2 | γ-Al$_2$O$_3$ | | 3.32 | | 3.6 | 310 | 0.35 | 41.5 | 0.145 |
| 148 | 0.4 | 0.4 | 1.2 | γ-Al$_2$O$_3$ | | 3.32 | | 3.6 | 320 | 0.49 | 39.5 | 0.194 |
| 149 | 0.5 | 0.5 | 1.5 | γ-Al$_2$O$_3$ | | 3.32 | | 3.6 | 300 | 0.19 | 49 | 0.093 |
| 150 | 0.5 | 0.5 | 1.5 | γ-Al$_2$O$_3$ | | 3.32 | | 3.6 | 310 | 0.29 | 45.5 | 0.132 |
| 151 | 0.5 | 0.5 | 1.5 | γ-Al$_2$O$_3$ | | 3.32 | | 3.6 | 320 | 0.41 | 43.5 | 0.178 |
| 152 | 0.6 | 0.6 | 1.8 | γ-Al$_2$O$_3$ | | 3.32 | | 3.6 | 300 | 0.19 | 52 | 0.099 |
| 153 | 0.6 | 0.6 | 1.8 | γ-Al$_2$O$_3$ | | 3.32 | | 3.6 | 310 | 0.29 | 49 | 0.142 |
| 154 | 0.6 | 0.6 | 1.8 | γ-Al$_2$O$_3$ | | 3.32 | | 3.6 | 320 | 0.43 | 44.4 | 0.191 |
| 155 | 0.7 | 0.7 | 2.1 | γ-Al$_2$O$_3$ | | 3.32 | | 3.6 | 300 | 0.21 | 47.24 | 0.099 |
| 156 | 0.7 | 0.7 | 2.1 | γ-Al$_2$O$_3$ | | 3.32 | | 3.6 | 310 | 0.29 | 43.71 | 0.127 |
| 157 | 0.7 | 0.7 | 2.1 | γ-Al$_2$O$_3$ | | 3.32 | | 3.6 | 320 | 0.41 | 40.5 | 0.166 |
| 158 | 0.8 | 0.8 | 2.4 | γ-Al$_2$O$_3$ | | 3.32 | | 3.6 | 300 | 0.29 | 34.85 | 0.101 |
| 159 | 0.8 | 0.8 | 2.4 | γ-Al$_2$O$_3$ | | 3.32 | | 3.6 | 310 | 0.46 | 27.81 | 0.128 |
| 160 | 0.8 | 0.8 | 2.4 | γ-Al$_2$O$_3$ | | 3.32 | | 3.6 | 320 | 0.66 | 23.9 | 0.158 |
| 161 | 0.7 | 0.7 | 2.1 | γ-Al$_2$O$_3$ | 10% USY (10) | 3.32 | | 3.6 | 300 | 0.24 | 51.3 | 0.123 |
| 162 | 0.7 | 0.7 | 2.1 | γ-Al$_2$O$_3$ | 10% USY (10) | 3.32 | | 3.6 | 310 | 0.36 | 47.44 | 0.171 |
| 163 | 0.7 | 0.7 | 2.1 | γ-Al$_2$O$_3$ | 10% USY (10) | 3.32 | | 3.6 | 320 | 0.51 | 44.54 | 0.227 |
| 164 | 0.7 | 0.7 | 2.1 | γ-Al$_2$O$_3$ | 10% USY (20) | 3.32 | | 3.6 | 300 | 0.24 | 51.98 | 0.125 |
| 165 | 0.7 | 0.7 | 2.1 | γ-Al$_2$O$_3$ | 10% USY (20) | 3.32 | | 3.6 | 310 | 0.33 | 50.88 | 0.168 |
| 166 | 0.7 | 0.7 | 2.1 | γ-Al$_2$O$_3$ | 10% USY (20) | 3.32 | | 3.6 | 320 | 0.48 | 48.32 | 0.232 |
| 167 | 0.7 | 0.7 | 2.1 | γ-Al$_2$O$_3$ | 10% USY (30) | 3.32 | | 3.6 | 300 | 0.22 | 50.12 | 0.110 |
| 168 | 0.7 | 0.7 | 2.1 | γ-Al$_2$O$_3$ | 10% USY (30) | 3.32 | | 3.6 | 310 | 0.32 | 48.34 | 0.155 |
| 169 | 0.7 | 0.7 | 2.1 | γ-Al$_2$O$_3$ | 10% USY (30) | 3.32 | | 3.6 | 320 | 0.47 | 43.65 | 0.205 |
| 170 | 0.7 | 0.7 | 2.1 | γ-Al$_2$O$_3$ | 10% USY (70) | 3.32 | | 3.6 | 300 | 0.26 | 48.84 | 0.127 |
| 171 | 0.7 | 0.7 | 2.1 | γ-Al$_2$O$_3$ | 10% USY (70) | 3.32 | | 3.6 | 310 | 0.39 | 45.37 | 0.177 |
| 172 | 0.7 | 0.7 | 2.1 | γ-Al$_2$O$_3$ | 10% USY (70) | 3.32 | | 3.6 | 320 | 0.56 | 41.78 | 0.234 |
| 173 | 0.6 | 0.6 | 1.8 | γ-Al$_2$O$_3$ | 10% USY (30) | 3.32 | | 3.6 | 300 | 0.21 | 51.85 | 0.109 |
| 174 | 0.6 | 0.6 | 1.8 | γ-Al$_2$O$_3$ | 10% USY (30) | 3.32 | | 3.6 | 310 | 0.3 | 52.29 | 0.157 |
| 175 | 0.6 | 0.6 | 1.8 | γ-Al$_2$O$_3$ | 10% USY (30) | 3.32 | | 3.6 | 320 | 0.44 | 49.25 | 0.217 |
| 176 | 0.6 | 0.6 | 1.8 | γ-Al$_2$O$_3$ | 20% USY (30) | 3.32 | | 3.6 | 300 | 0.17 | 58.5 | 0.099 |
| 177 | 0.6 | 0.6 | 1.8 | γ-Al$_2$O$_3$ | 20% USY (30) | 3.32 | | 3.6 | 310 | 0.26 | 57.23 | 0.149 |
| 178 | 0.6 | 0.6 | 1.8 | γ-Al$_2$O$_3$ | 20% USY (30) | 3.32 | | 3.6 | 320 | 0.38 | 54.38 | 0.207 |

TABLE 24-continued

| | Composition of components of bimetallic oxide (A): AmBnOx Ratio between m, n, and x | | | Support | Solid acid | Composition of oxidizing gas (vol %) | | | Reaction temperature | CH₄ Conversion ratio | HCHO Selectivity | HCHO Yield |
|---|---|---|---|---|---|---|---|---|---|---|---|---|
| Example | Pd | Ru | O | (B) | (D) | CH₄ | NO | O₂ | (° C.) | (%) | (%) | (%) |
| 179 | 0.6 | 0.6 | 1.8 | γ-Al₂O₃ | 20% USY (30) | 3.32 | | 3.6 | 330 | 0.55 | 49.33 | 0.271 |
| 180 | 0.6 | 0.6 | 1.8 | γ-Al₂O₃ | 20% USY (10) | 3.32 | | 3.6 | 300 | 0.16 | 54.6 | 0.087 |
| 181 | 0.6 | 0.6 | 1.8 | γ-Al₂O₃ | 20% USY (10) | 3.32 | | 3.6 | 310 | 0.246 | 52.28 | 0.129 |
| 182 | 0.6 | 0.6 | 1.8 | γ-Al₂O₃ | 20% USY (10) | 3.32 | | 3.6 | 320 | 0.36 | 49.31 | 0.178 |
| 183 | 0.6 | 0.6 | 1.8 | γ-Al₂O₃ | 30% USY (30) | 3.32 | | 3.6 | 300 | 0.19 | 46.23 | 0.088 |
| 184 | 0.6 | 0.6 | 1.8 | γ-Al₂O₃ | 30% USY (30) | 3.32 | | 3.6 | 310 | 0.26 | 47.43 | 0.123 |
| 185 | 0.6 | 0.6 | 1.8 | γ-Al₂O₃ | 30% USY (30) | 3.32 | | 3.6 | 320 | 0.38 | 45.86 | 0.174 |

Supported catalyst 0.5 g,
Reaction pressure 0.1 MPa

TABLE 25

| | Composition of components of bimetallic oxide (A): AmBnOx Ratio between m, n, and x | | | Support | Solid acid | Composition of oxidizing gas (vol %) | | | Reaction temperature | CH₄ Conversion ratio | HCHO Selectivity | HCHO Yield | Amount of Catalyst used |
|---|---|---|---|---|---|---|---|---|---|---|---|---|---|
| Example | Pd | Ru | O | (B) | (D) | CH₄ | NO | O₂ | (° C.) | (%) | (%) | (%) | (g) |
| 191 | 0.6 | 0.6 | 1.8 | γ-Al₂O₃ | 30% USY (30) | 1.6 | | 1.6 | 300 | 0.13 | 43.57 | 0.057 | 0.25 |
| 192 | 0.6 | 0.6 | 1.8 | γ-Al₂O₃ | 30% USY (30) | 1.6 | | 1.6 | 310 | 0.21 | 41.9 | 0.088 | 0.25 |
| 193 | 0.6 | 0.6 | 1.8 | γ-Al₂O₃ | 30% USY (30) | 1.6 | | 1.6 | 320 | 0.32 | 39.36 | 0.126 | 0.25 |
| 194 | 0.6 | 0.6 | 1 8 | γ-Al₂O₃ | 30% USY (30) | 1.6 | | 1.6 | 300 | 0.25 | 48.4 | 0.121 | 0.5 |
| 195 | 0.6 | 0.6 | 1.8 | γ-Al₂O₃ | 30% USY (30) | 1.6 | | 1.6 | 310 | 0.37 | 45.5 | 0.168 | 0.5 |
| 196 | 0.6 | 0.6 | 1.8 | γ-Al₂O₃ | 30% USY (30) | 1.6 | | 1.6 | 320 | 0.54 | 42.2 | 0.228 | 0.5 |
| 197 | 0.6 | 0.6 | 1.8 | γ-Al₂O₃ | 30% USY (30) | 1.6 | | 1.6 | 300 | 0.31 | 48.04 | 0.149 | 0.75 |
| 198 | 0.6 | 0.6 | 1.8 | γ-Al₂O₃ | 30% USY (30) | 1.6 | | 1.6 | 310 | 0.47 | 44.35 | 0.208 | 0.75 |
| 199 | 0.6 | 0.6 | 1.8 | γ-Al₂O₃ | 30% USY (30) | 1.6 | | 1.6 | 320 | 0.68 | 39.58 | 0.269 | 0.75 |

Reaction pressure 0.1 MPa

TABLE 26

| | Composition of components of bimetallic oxide (A): AmBnOx Ratio between m, n, and x | | | Support | Solid acid | Composition of oxidizing gas (vol %) | | | Reaction temperature | CH₄ Conversion ratio | HCHO Selectivity | HCHO Yield |
|---|---|---|---|---|---|---|---|---|---|---|---|---|
| Example | Pd | Ru | O | (B) | (D) | CH₄ | NO | O₂ | (° C.) | (%) | (%) | (%) |
| 201 | 0.6 | 0.6 | 1.8 | γ-Al₂O₃ | | 3.32 | | 3.6 | 300 | 0.19 | 52 | 0.099 |
| 202 | 0.6 | 0.6 | 1.8 | γ-Al₂O₃ | | 3.32 | | 3.6 | 310 | 0.29 | 49 | 0.142 |
| 203 | 0.6 | 0.6 | 1.8 | γ-Al₂O₃ | | 3.32 | | 3.6 | 320 | 0.43 | 44.4 | 0.191 |
| 204 | 0.6 | 0.6 | 1.8 | γ-Al₂O₃ | 20% ZSM-5 (50) | 3.32 | | 3.6 | 300 | 0.2 | 56.55 | 0.113 |
| 205 | 0.6 | 0.6 | 1.8 | γ-Al₂O₃ | 20% ZSM-5 (50) | 3.32 | | 3.6 | 310 | 0.3 | 52.87 | 0.159 |
| 206 | 0.6 | 0.6 | 1.8 | γ-Al₂O₃ | 20% ZSM-5 (50) | 3.32 | | 3.6 | 320 | 0.44 | 48.14 | 0.212 |
| 207 | 0.6 | 0.6 | 1.8 | γ-Al₂O₃ | 20% ZSM-5 (80) | 3.32 | | 3.6 | 300 | 0.24 | 55.22 | 0.133 |
| 208 | 0.6 | 0.6 | 1.8 | γ-Al₂O₃ | 20% ZSM-5 (80) | 3.32 | | 3.6 | 310 | 0.35 | 52.86 | 0.185 |
| 209 | 0.6 | 0.6 | 1.8 | γ-Al₂O₃ | 20% ZSM-5 (80) | 3.32 | | 3.6 | 320 | 0.52 | 48.4 | 0.252 |
| 210 | 0.6 | 0.6 | 1.8 | γ-Al₂O₃ | 20% ZSM-5 (280) | 3.32 | | 3.6 | 300 | 0.2 | 55.22 | 0.110 |
| 211 | 0.6 | 0.6 | 1.8 | γ-Al₂O₃ | 20% ZSM-5 (280) | 3.32 | | 3.6 | 310 | 0.3 | 53.7 | 0.161 |
| 212 | 0.6 | 0.6 | 1.8 | γ-Al₂O₃ | 20% ZSM-5 (280) | 3.32 | | 3.6 | 320 | 0.43 | 50.28 | 0.216 |
| 213 | 0.6 | 0.6 | 1.8 | γ-Al₂O₃ | 20% ZSM-5 (280) | 3.32 | | 3.6 | 330 | 0.63 | 46.1 | 0.290 |

Supported catalyst 0.5 g,
Reaction pressure 0.1 MPa

TABLE 27

| | Composition of components of bimetallic oxide (A): AmBnOx Ratio between m, n, and x | | | Support | Solid acid | Composition of oxidizing gas (vol %) | | | Reaction temperature | CH₄ Conversion ratio | HCHO Selectivity | HCHO Yield | Reaction pressure |
|---|---|---|---|---|---|---|---|---|---|---|---|---|---|
| Example | Pd | Ru | O | (B) | (D) | CH₄ | NO | O₂ | (° C.) | (%) | (%) | (%) | (MPa) |
| 221 | 0.6 | 0.6 | 1.8 | γ-Al₂O₃ | | 3.32 | | 3.6 | 240 | 0.09 | 46.75 | 0.043 | 0.4 |
| 222 | 0.6 | 0.6 | 1.8 | γ-Al₂O₃ | | 3.32 | | 3.6 | 260 | 0.08 | 45.00 | 0.034 | 0.1 |
| 223 | 0.6 | 0.6 | 1.8 | γ-Al₂O₃ | | 3.32 | | 3.6 | 260 | 0.09 | 48.00 | 0.044 | 0.2 |
| 224 | 0.6 | 0.6 | 1.8 | γ-Al₂O₃ | | 3.32 | | 3.6 | 260 | 0.15 | 49.00 | 0.074 | 0.3 |
| 225 | 0.6 | 0.6 | 1.8 | γ-Al₂O₃ | | 3.32 | | 3.6 | 260 | 0.21 | 44.04 | 0.094 | 0.4 |
| 226 | 0.6 | 0.6 | 1.8 | γ-Al₂O₃ | | 3.32 | | 3.6 | 280 | 0.14 | 50.16 | 0.068 | 0.1 |
| 227 | 0.6 | 0.6 | 1.8 | γ-Al₂O₃ | | 3.32 | | 3.6 | 280 | 0.22 | 51.60 | 0.114 | 0.2 |

Supported catalyst 0.5 g

TABLE 28

| | Composition of components of bimetallic oxide (A): AmBnOx Ratio between m, n, and x | | | Support | Solid acid | Composition of oxidizing gas (vol %) | | | Reaction temperature | CH₄ Conversion ratio | HCHO Selectivity | HCHO Yield |
|---|---|---|---|---|---|---|---|---|---|---|---|---|
| Example | Pd | Ru | O | (B) | (D) | CH₄ | NO | O₂ | (° C.) | (%) | (%) | (%) |
| 231 | 0.6 | 0.6 | 1.8 | η-Al₂O₃ | | 13.4 | | 0.7 | 300 | 0.08 | 66 | 0.053 |
| 232 | 0.6 | 0.6 | 1.8 | η-Al₂O₃ | 10% USY (10) | 13.4 | | 0.7 | 300 | 0.11 | 60 | 0.066 |
| 233 | 0.6 | 0.6 | 1.8 | η-Al₂O₃ | 10% USY (10) | 13.4 | | 0.7 | 280 | 0.05 | 65 | 0.033 |
| 234 | 0.6 | 0.6 | 1.8 | η-Al₂O₃ | 20% USY (10) | 13.4 | | 0.7 | 280 | 0.06 | 62 | 0.037 |
| 235 | 0.6 | 0.6 | 1.8 | η-Al₂O₃ | 30% USY (10) | 13.4 | | 0.7 | 280 | 0.06 | 56 | 0.034 |
| 236 | 0.6 | 0.6 | 1.8 | η-Al₂O₃ | 10% USY (10) | 13.4 | | 0.7 | 300 | 0.08 | 66 | 0.053 |
| 237 | 0.6 | 0.6 | 1.8 | η-Al₂O₃ | 10% USY (10) | 13.4 | | 0.7 | 300 | 0.11 | 60 | 0.066 |
| 238 | 0.6 | 0.6 | 1.8 | η-Al₂O₃ | 10% USY (10) | 13.4 | | 0.35 | 300 | 0.09 | 64 | 0.058 |
| 239 | 0.6 | 0.6 | 1.8 | η-Al₂O₃ | 10% USY (10) | 13.4 | | 0.15 | 300 | 0.08 | 65 | 0.052 |
| 240 | 0.4 | 0.4 | 1.2 | ZSM-5 (50) | | 13.4 | | 0.7 | 300 | 0.08 | 32 | 0.026 |
| 241 | 0.4 | 0.4 | 1.2 | ZSM-5 (80) | | 13.4 | | 0.7 | 300 | 0.07 | 47 | 0.033 |
| 242 | 0.4 | 0.4 | 1.2 | ZSM-5 (280) | | 13.4 | | 0.7 | 300 | 0.03 | 31 | 0.009 |
| 243 | 0.4 | 0.4 | 1.2 | ZSM-5 (50) | | 13.4 | | 0.7 | 300 | 0.08 | 32 | 0.026 |
| 244 | 0.5 | 0.5 | 1.5 | ZSM-5 (50) | | 13.4 | | 0.7 | 300 | 0.07 | 33 | 0.023 |
| 245 | 0.6 | 0.6 | 1.8 | ZSM-5 (50) | | 13.4 | | 0.7 | 300 | 0.07 | 37 | 0.026 |

Supported catalyst 0.5 g,
Reaction pressure 0.1 MPa

TABLE 29

| | Composition of components of bimetallic oxide (A): AmBnOx Ratio between m, n, and x | | | Support | Solid acid | Composition of oxidizing gas (vol %) | | | Reaction temperature | CH₄ Conversion ratio | HCHO Selectivity | HCHO Yield |
|---|---|---|---|---|---|---|---|---|---|---|---|---|
| Example | Pd | Ru | O | (B) | (D) | CH₄ | NO | O₂ | (° C.) | (%) | (%) | (%) |
| 251 | 0.4 | 0.4 | 1.2 | ZSM-5 (50) | | 13.4 | 1.7 | 0.7 | 275 | 0.05 | 72.00 | 0.036 |
| 252 | 0.4 | 0.4 | 1.2 | ZSM-5 (50) | | 13.4 | 1.7 | 0.7 | 280 | 0.06 | 72.15 | 0.043 |
| 253 | 0.4 | 0.4 | 1.2 | ZSM-5 (50) | | 13.4 | 1.7 | 0.7 | 285 | 0.07 | 70.80 | 0.050 |
| 254 | 0.4 | 0.4 | 1.2 | ZSM-5 (50) | | 13.4 | 1.7 | 0.7 | 290 | 0.09 | 68.99 | 0.062 |
| 255 | 0.4 | 0.4 | 1.2 | ZSM-5 (50) | | 13.4 | 1.7 | 0.7 | 295 | 0.10 | 68.87 | 0.069 |
| 256 | 0.4 | 0.4 | 1.2 | ZSM-5 (50) | | 13.4 | 1.7 | 0.7 | 300 | 0.14 | 62.00 | 0.087 |
| 257 | 0.4 | 0.4 | 1.2 | η-Al₂O₃ | | 13.4 | 1.7 | 0.7 | 280 | 0.05 | 56.00 | 0.028 |
| 258 | 0.4 | 0.4 | 1.2 | η-Al₂O₃ | | 13.4 | 1.7 | 0.7 | 290 | 0.07 | 56.00 | 0.039 |
| 259 | 0.4 | 0.4 | 1.2 | η-Al₂O₃ | | 13.4 | 1.7 | 0.7 | 300 | 0.10 | 56.00 | 0.056 |
| 260 | 0.4 | 0.4 | 1.2 | η-Al₂O₃ | | 13.4 | 1.7 | 0.7 | 310 | 0.15 | 55.00 | 0.083 |
| 261 | 0.4 | 0.4 | 1.2 | USY (30) | | 13.4 | 1.7 | 0.7 | 300 | 0.03 | 43.00 | 0.013 |
| 262 | 0.4 | 0.4 | 1.2 | USY (30) | | 13.4 | 1.7 | 0.7 | 310 | 0.04 | 45.62 | 0.018 |

TABLE 29-continued

| Example | Pd | Ru | O | Support (B) | Solid acid (D) | CH$_4$ | NO | O$_2$ | Reaction temperature (° C.) | CH$_4$ Conversion ratio (%) | HCHO Selectivity (%) | HCHO Yield (%) |
|---|---|---|---|---|---|---|---|---|---|---|---|---|
| 263 | 0.4 | 0.4 | 1.2 | USY (30) | | 13.4 | 1.7 | 0.7 | 320 | 0.05 | 43.90 | 0.022 |
| 264 | 0.4 | 0.4 | 1.2 | USY (30) | | 13.4 | 1.7 | 0.7 | 330 | 0.08 | 41.41 | 0.033 |
| 265 | 0.6 | 0.6 | 1.8 | ZSM-5 (50) | | 13.4 | 1.7 | 0.7 | 285 | 0.05 | 66.00 | 0.033 |
| 266 | 0.6 | 0.6 | 1.8 | ZSM-5 (50) | | 13.4 | 1.7 | 0.7 | 290 | 0.07 | 60.80 | 0.043 |
| 267 | 0.6 | 0.6 | 1.8 | ZSM-5 (50) | | 13.4 | 1.7 | 0.7 | 295 | 0.08 | 60.52 | 0.048 |
| 268 | 0.6 | 0.6 | 1.8 | ZSM-5 (50) | | 13.4 | 1.7 | 0.7 | 300 | 0.09 | 59.72 | 0.054 |
| 269 | 0.4 | 0.4 | 1.2 | USY (30) | | 13.4 | | 0.7 | 300 | 0.05 | 23.00 | 0.012 |
| 270 | 0.4 | 0.4 | 1.2 | USY (30) | | 13.4 | | 0.7 | 310 | 0.06 | 28.04 | 0.017 |
| 271 | 0.4 | 0.4 | 1.2 | USY (30) | | 13.4 | | 0.7 | 320 | 0.07 | 29.99 | 0.021 |
| 272 | 0.4 | 0.4 | 1.2 | β (38) | | 13.4 | | 0.7 | 280 | 0.04 | 39.00 | 0.016 |
| 273 | 0.4 | 0.4 | 1.2 | β (38) | | 13.4 | | 0.7 | 300 | 0.09 | 41.00 | 0.037 |
| 274 | 0.2 | 0.2 | 0.6 | SiO$_2$ | 50% ZSM-5 (50) | 6.7 | 1.7 | 0.4 | 240 | 0.04 | 66.00 | 0.026 |
| 275 | 0.2 | 0.2 | 0.6 | SiO$_2$ | 50% ZSM-5 (50) | 6.7 | 1.7 | 0.4 | 250 | 0.05 | 60.00 | 0.030 |
| 276 | 0.2 | 0.2 | 0.6 | SiO$_2$ | 50% ZSM-5 (50) | 6.7 | 1.7 | 0.4 | 260 | 0.06 | 54.00 | 0.032 |
| 277 | 0.3 | 0.3 | 0.9 | SiO$_2$ | 50% ZSM-5 (50) | 6.7 | 1.7 | 0.4 | 250 | 0.03 | 58 | 0.017 |
| 278 | 0.3 | 0.3 | 0.9 | SiO$_2$ | 50% ZSM-5 (50) | 6.7 | 1.7 | 0.4 | 260 | 0.03 | 61 | 0.018 |
| 279 | 0.3 | 0.3 | 0.9 | SiO$_2$ | 50% ZSM-5 (50) | 6.7 | 1.7 | 0.4 | 270 | 0.05 | 63 | 0.032 |

Supported catalyst 0.5 g,
Reaction pressure 0.1 MPa

TABLE 30

| Example | Pd | Ru | O | Support (B) | Solid acid (D) | CH$_4$ | NO | O$_2$ | Reaction temperature (° C.) | CH$_4$ Conversion ratio (%) | HCHO Selectivity (%) | HCHO Yield (%) |
|---|---|---|---|---|---|---|---|---|---|---|---|---|
| 291 | 0.3 | 0.3 | 0.9 | η-Al$_2$O$_3$ | | 13.4 | 1.7 | 0.7 | 300 | 0.08 | 60.00 | 0.048 |
| 292 | 0.4 | 0.4 | 1.2 | η-Al$_2$O$_3$ | | 13.4 | 1.7 | 0.7 | 300 | 0.10 | 56.24 | 0.056 |
| 293 | 0.5 | 0.5 | 1.5 | η-Al$_2$O$_3$ | | 13.4 | 1.7 | 0.7 | 300 | 0.1 | 54 | 0.054 |
| 294 | 0.6 | 0.6 | 1.8 | η-Al$_2$O$_3$ | | 13.4 | 1.7 | 0.7 | 300 | 0.1 | 56 | 0.056 |
| 295 | 0.7 | 0.7 | 2.1 | η-Al$_2$O$_3$ | | 13.4 | 1.7 | 0.7 | 300 | 0.1 | 57 | 0.057 |
| 296 | 0.6 | 0.6 | 1.8 | η-Al$_2$O$_3$ | | 13.4 | 1.7 | 0.7 | 295 | 0.08 | 58 | 0.046 |
| 297 | 0.6 | 0.6 | 1.8 | η-Al$_2$O$_3$ | | 13.4 | 1.7 | 0.7 | 300 | 0.1 | 56 | 0.056 |
| 298 | 0.6 | 0.6 | 1.8 | η-Al$_2$O$_3$ | | 13.4 | 1.7 | 0.7 | 305 | 0.11 | 58 | 0.064 |
| 299 | 0.4 | 0.4 | 1.2 | η-Al$_2$O$_3$ | | 13.4 | 1.7 | 0.7 | 300 | 0.10 | 56.24 | 0.056 |
| 300 | 0.4 | 0.4 | 1.2 | η-Al$_2$O$_3$ | 5% ZSM-5 (50) | 13.4 | 1.7 | 0.7 | 300 | 0.11 | 55.26 | 0.061 |
| 301 | 0.4 | 0.4 | 1.2 | η-Al$_2$O$_3$ | 30% ZSM-5 (50) | 13.4 | 1.7 | 0.7 | 300 | 0.12 | 55.00 | 0.066 |
| 302 | 0.6 | 0.6 | 1.8 | η-Al$_2$O$_3$ | | 13.4 | 1.7 | 0.7 | 300 | 0.1 | 56 | 0.056 |
| 303 | 0.6 | 0.6 | 1.8 | η-Al$_2$O$_3$ | 10% ZSM-5 (50) | 13.4 | 1.7 | 0.7 | 300 | 0.1 | 58 | 0.058 |
| 304 | 0.6 | 0.6 | 1.8 | η-Al$_2$O$_3$ | 20% ZSM-5 (50) | 13.4 | 1.7 | 0.7 | 300 | 0.11 | 56 | 0.062 |
| 305 | 0.6 | 0.6 | 1.8 | η-Al$_2$O$_3$ | 30% ZSM-5 (50) | 13.4 | 1.7 | 0.7 | 300 | 0.14 | 56 | 0.078 |
| 306 | 0.6 | 0.6 | 1.8 | η-Al$_2$O$_3$ | | 13.4 | 1.7 | 0.7 | 300 | 0.1 | 56 | 0.056 |
| 307 | 0.6 | 0.6 | 1.8 | η-Al$_2$O$_3$ | 10% USY (70) | 13.4 | 1.7 | 0.7 | 300 | 0.1 | 61 | 0.061 |
| 308 | 0.6 | 0.6 | 1.8 | η-Al$_2$O$_3$ | 10% USY (30) | 13.4 | 1.7 | 0.7 | 300 | 0.12 | 59 | 0.071 |
| 309 | 0.6 | 0.6 | 1.8 | η-Al$_2$O$_3$ | 10% USY (20) | 13.4 | 1.7 | 0.7 | 300 | 0.13 | 59 | 0.077 |
| 310 | 0.6 | 0.6 | 1.8 | η-Al$_2$O$_3$ | 10% USY (10) | 13.4 | 1.7 | 0.7 | 300 | 0.13 | 60 | 0.078 |
| 311 | 0.3 | 0.3 | 0.9 | TiO$_2$ | | 13.4 | 1.7 | 0.7 | 300 | 0.05 | 42 | 0.021 |
| 312 | 0.3 | 0.3 | 0.9 | TiO$_2$ | 5% ZSM-5 (50) | 13.4 | 1.7 | 0.7 | 300 | 0.06 | 43 | 0.026 |
| 313 | 0.3 | 0.3 | 0.9 | TiO$_2$ | 10% ZSM-5 (50) | 13.4 | 1.7 | 0.7 | 300 | 0.09 | 43 | 0.039 |

Supported catalyst 0.5 g,
Reaction pressure 0.1 MPa

45

46

The invention claimed is:

1. A method for partially oxidizing an alkane, comprising contacting an alkane with a supported catalyst in a presence of an oxidizer to convert the alkane into an aldehyde, wherein the supported catalyst comprises a bimetallic oxide carried on a support, and the bimetallic oxide is represented by the following formula and comprises oxygen and two metals selected from metals of groups 8 to 10 of the periodic table:

$$A_m B_n O_x$$

wherein the bimetallic oxide and the support are each a metal selected from metallic elements of groups 8 to 10 of the periodic table; the bimetallic oxide and the support are not the same metallic element; m, n, and x mean amounts ((mmol)) of the bimetallic oxide, the support, and oxygen, respectively, per 1 g of the supported catalyst; m is more than 0 [mmol/g-cat] and less than 1 [mmol/g-cat]; n is more than 0 [mmol/g-cat] and less than 1 [mmol/g-cat]; and x is a value [mmol/g-cat] satisfying oxidation states of the bimetallic oxide and the support.

2. The method for partially oxidizing an alkane according to claim 1, wherein the two metals selected from metals of groups 8 to 10 of the periodic table are two metals selected from palladium, ruthenium, iridium, and platinum.

3. The method for partially oxidizing an alkane according to claim 1, wherein the contacting of the alkane is performed further in a presence of a solid acid.

4. The method for partially oxidizing an alkane according to claim 1, wherein the support is at least one support selected from zeolite, $Al_2O_3$, $TiO_2$, $ZrO_2$, $CeO_2$, $SiO_2$, and $SiO_2$—$Al_2O_3$.

5. The method for partially oxidizing an alkane according to claim 1, wherein the alkane is methane, and the aldehyde is formaldehyde.

6. The method for partially oxidizing an alkane according to claim 1, wherein the oxidizer is at least one oxidizer selected from oxygen, nitrogen monoxide, and nitrogen dioxide.

7. The method for partially oxidizing an alkane according to claim 1, wherein the partially oxidizing is performed at a temperature of 235 to 350° C.

8. The method for partially oxidizing an alkane according to claim 1, wherein a hybrid catalyst comprising the supported catalyst with a solid acid is used.

9. The method for partially oxidizing an alkane according to claim 8, wherein the ratio of the solid acid is 5 to 60 mass % based on 100 mass % in total of the supported catalyst and the solid acid.

10. The method for partially oxidizing an alkane according to claim 8, wherein the support of the supported catalyst is at least one selected from $Al_2O_3$, $TiO_2$, $ZrO_2$, $CeO_2$, $SiO_2$, and $SiO_2$—$Al_2O_3$, and the solid acid is at least one selected from ZMS-5 zeolite and USY zeolite; or the support of the supported catalyst is ZMS-5 zeolite, and the solid acid is at least one of $Al_2O_3$ or $ZrO_2$.

* * * * *